US010792446B1

(12) United States Patent
Baek et al.

(10) Patent No.: US 10,792,446 B1
(45) Date of Patent: Oct. 6, 2020

(54) COMPACT SPACER FOR METERED DOSE INHALER

(71) Applicant: Blue Ocean Group, LLC, Irvine, CA (US)

(72) Inventors: Simon Baek, Irvine, CA (US); Cindy Baek, Irvine, CA (US); Andrew March, Irvine, CA (US)

(73) Assignee: Blue Ocean Group, LLC, Irvine, CA (US)

( * ) Notice: Subject to any disclaimer, the term of this patent is extended or adjusted under 35 U.S.C. 154(b) by 0 days.

(21) Appl. No.: 16/902,367

(22) Filed: Jun. 16, 2020

Related U.S. Application Data

(63) Continuation of application No. 16/882,449, filed on May 23, 2020.

(60) Provisional application No. 62/852,792, filed on May 24, 2019.

(51) Int. Cl.
*A61M 15/00* (2006.01)

(52) U.S. Cl.
CPC .... *A61M 15/0086* (2013.01); *A61M 15/0001* (2014.02); *A61M 15/009* (2013.01); *A61M 15/0025* (2014.02)

(58) Field of Classification Search
CPC .......... A61M 15/0021; A61M 15/0025; A61M 15/0026; A61M 15/009; A61M 15/0013; A61M 15/0086; A61M 15/0088
See application file for complete search history.

(56) References Cited

U.S. PATENT DOCUMENTS

| | | | | | |
|---|---|---|---|---|---|
| 3,151,618 | A | * | 10/1964 | Wakeman | A61M 15/009 128/200.23 |
| 3,191,867 | A | * | 6/1965 | Helms | A61M 15/009 239/288.5 |
| 3,994,421 | A | * | 11/1976 | Hansen | A61M 15/0086 222/182 |
| 4,637,528 | A | * | 1/1987 | Wachinski | B65D 83/44 128/200.23 |
| 4,641,644 | A | * | 2/1987 | Andersson | A61M 15/0088 128/200.23 |

(Continued)

OTHER PUBLICATIONS

Search Report by the USPTO dated Aug. 18, 2020 for application PCT/US20/34428.

(Continued)

*Primary Examiner* — Michael J Tsai
(74) *Attorney, Agent, or Firm* — Ryuh Patent Law; Steven Yu

(57) ABSTRACT

A spacer device for use with a metered dose inhaler (MDI). The spacer device comprises an aerosol chamber for holding the aerosolized medication sprayed from the MDI. According to one particular design, the aerosol chamber has a forward shell, a rear shell, and an extendable barrel in between. The extendable barrel comprises a flexible plastic sheath that is supported by a coiled wire spring. The spacer device further comprises a mounting bracket to hold the MDI. The mounting bracket holds the MDI such that the spray outlet of the MDI is mated with the aerosol chamber. Also, the assembly is configured such that the aerosol chamber is aligned substantially parallel to the actuator boot of the MDI. During use, the aerosol chamber is folded downward away from the MDI. The aerosol chamber is then extended outward to increase its volume.

20 Claims, 16 Drawing Sheets

(56) References Cited

U.S. PATENT DOCUMENTS

| | | | | | |
|---|---|---|---|---|---|
| 5,505,194 | A * | 4/1996 | Adjei | ............... | A61M 15/0086 128/200.23 |
| 5,571,246 | A * | 11/1996 | Alldredge | ......... | A61M 15/0086 128/200.14 |
| 6,230,704 | B1 * | 5/2001 | Durkin | ............. | A61M 15/0086 128/200.22 |
| 6,293,279 | B1 * | 9/2001 | Schmidt | ........... | A61M 15/0086 128/200.23 |
| 6,345,617 | B1 * | 2/2002 | Engelbreth | ......... | A61M 11/002 128/200.23 |
| 6,595,206 | B2 * | 7/2003 | Vito | .................. | A61M 15/0086 128/200.23 |
| 7,360,537 | B2 * | 4/2008 | Snyder | ............. | A61M 15/0086 128/200.23 |
| 7,832,393 | B2 * | 11/2010 | Vito | .................. | A61M 15/0026 128/200.23 |
| 9,364,622 | B2 * | 6/2016 | Steelman | ......... | A61M 15/0013 |
| 2002/0121276 | A1 * | 9/2002 | Genova | ............ | A61M 15/0096 128/200.23 |
| 2005/0126561 | A1 * | 6/2005 | Grychowski | ....... | A61M 16/208 128/200.23 |
| 2007/0074718 | A1 * | 4/2007 | Austin | ................ | A61M 15/009 128/200.23 |
| 2008/0087279 | A1 * | 4/2008 | Tieck | ................... | A61M 11/001 128/200.23 |
| 2016/0045686 | A1 * | 2/2016 | Jaroslavsky | ...... | A61M 15/0021 128/200.23 |

OTHER PUBLICATIONS

Written Opinion by the USPTO dated Aug. 18, 2020 for application PCT/US20/34428.

* cited by examiner

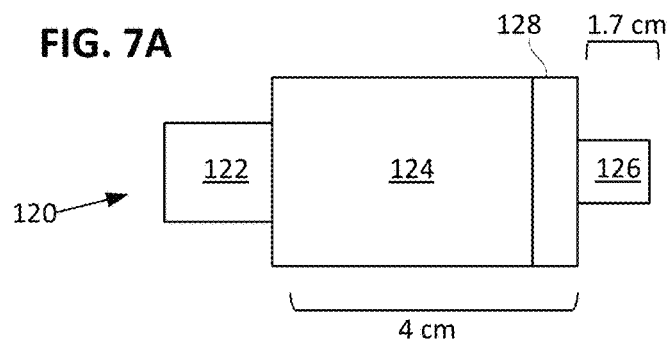
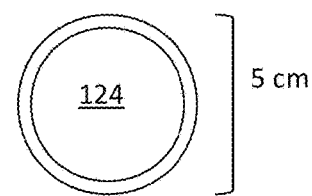
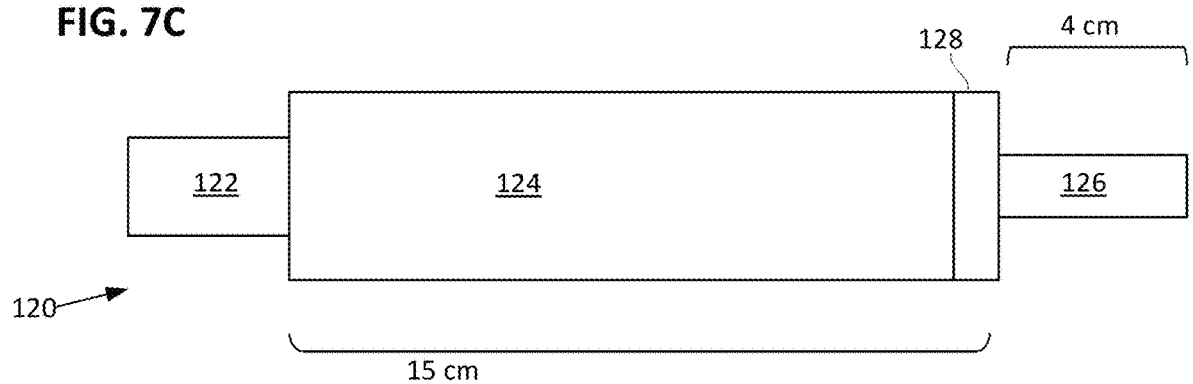
FIG. 7A
FIG. 7B
FIG. 7C
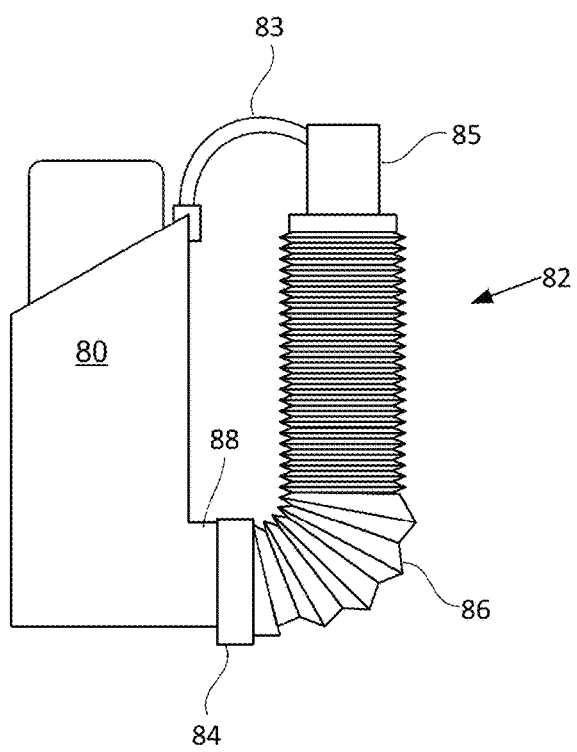
FIG. 8

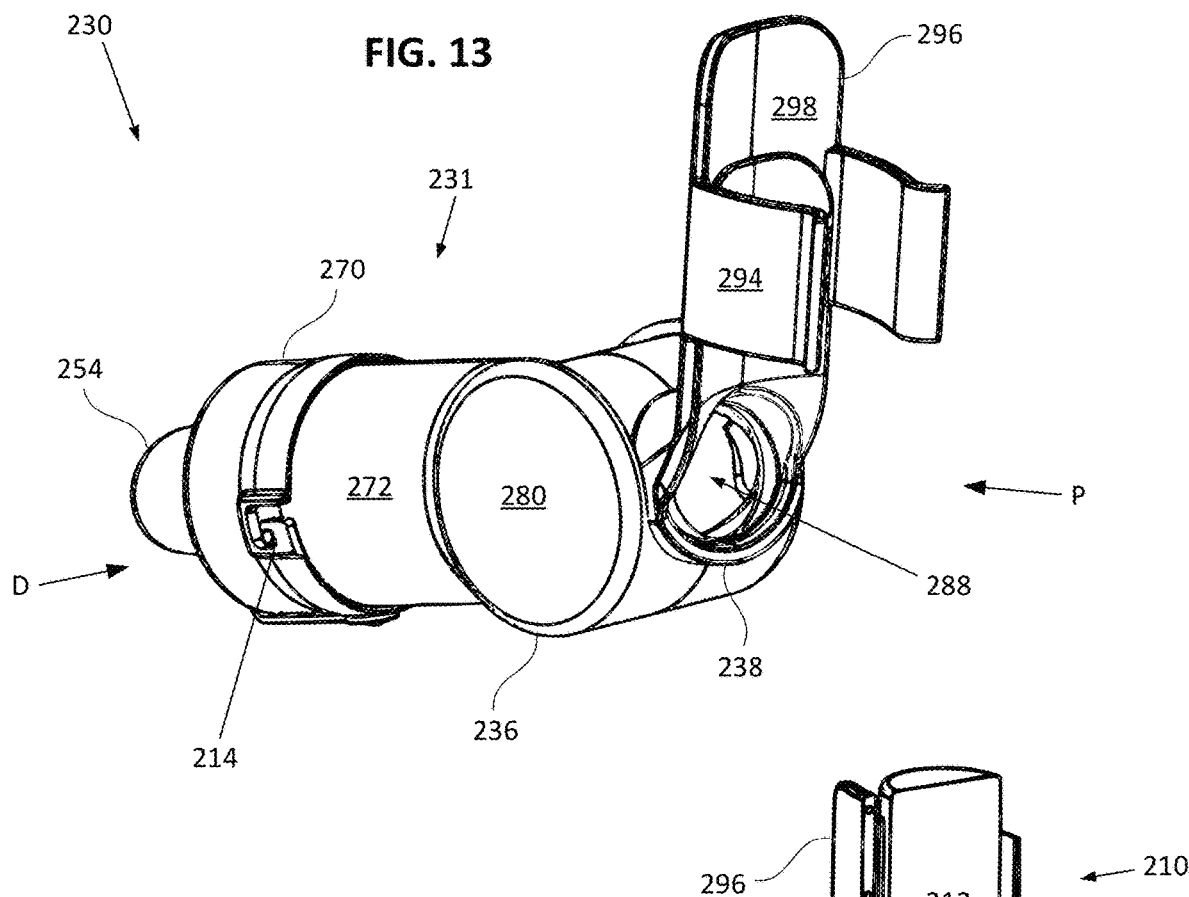

COMPACT SPACER FOR METERED DOSE INHALER

TECHNICAL FIELD

This invention relates to spacer devices for metered dose inhalers for administering medications.

BACKGROUND

Metered dose inhalers (MDI) are used for administering medications, such as bronchodilator drugs and corticosteroids, to the lungs. FIG. 1 shows an example of a metered dose inhaler 10 and its mechanism of action. The metered dose inhaler 10 comprises a pressurized medication canister 12 and an actuator 19, which holds the canister 12. The actuator 19 comprises a boot portion 14 for holding the canister 12, a spray nozzle 15, and a mouthpiece 16, which is also the outlet for the aerosol spray 18.

The canister 12 holds a reservoir 17 of medication and is pressurized with a propellant. A metering valve 13 is located at the bottom of the canister 12 and the medication flows out through a stem 11. The user loads the canister 12 into the boot portion 14 of the actuator 19 such that the stem 11 fits into the spray nozzle 15. When the user presses down on the canister 12, the valve stem 11 presses into the spray nozzle 15, causing it to discharge a preset amount of medication as an aerosolized spray 18 out of the mouthpiece 16 for delivery into the user's lung. When working properly, the user inhales the aerosolized medication 18 through the mouth and into the bronchial passageways of the lungs.

However, MDIs are not very efficient at drug delivery; they deliver only about 10% of the dose to the lungs, with the rest being deposited elsewhere, such as the oropharynx. This is because pressurized MDIs generate an aerosol spray with a velocity that is faster than the patient can inhale. This puts a lot of demand on the users' performance to synchronize their inhalation with the spray actuation in order to release the aerosol spray at the beginning of inhalation. This problem is particularly acute in children and the elderly. With the lack of proper synchronization, instead of being inhaled into the lung, much of the sprayed medication may be deposited onto the back of the mouth or pharynx. In addition to loss of therapeutic effectiveness, this can cause cough, voice hoarseness, fungal infections, and absorption of the medication into the bloodstream.

Because of these difficulties, many patients are advised to use a spacer that is fitted to the mouthpiece of the MDI to overcome some of the problems of poor coordination and oropharyngeal deposition. Spacers work by lengthening the distance between the actuator mouthpiece and the user's mouth, thus giving the user more time to synchronize inhalation and reducing the impaction onto the oropharynx. Also, evaporation of spray solvent would decrease the size of particles, facilitating more deposition in the lungs and better penetration to peripheral airways.

FIG. 2 shows an example of a conventional spacer device 20 of the prior art. The spacer 20 comprises a barrel-shaped chamber 22, a mouthpiece 24 at the front, a one-way valve 28, and a socket opening 26 at the back for fitting the inhaler outlet/mouthpiece. In use, the inhaler mouthpiece is fitted into the socket opening 26 at the back of the spacer 20. The user puts their mouth on the mouthpiece 24 at the front the spacer 20. When the user actuates the metered dose inhaler, the aerosol spray is discharged into the chamber 22 and suspended momentarily therein. The user then inhales the aerosolized medication suspended in the chamber 22 by breathing in and out.

The one-way valve 28 allows the user to inhale the medication through the spacer 20. In case the user exhales, the one-way valve 28 would act to divert the exhaled breath outward rather than entering the chamber 22. Some spacers are also equipped with a whistle as a flow rate indicator, i.e. making a whistling sound if the user is inhaling too quickly.

Yet, there are still problems with existing spacers. There is a tradeoff between size and effectiveness. Spacers can have a compact design, but those are too short and small to be effective. More complex spacer designs, such as the valved holding chambers (VHC), have a wider and longer barrel to improve drug delivery effectiveness, but the problem is that they are too bulky, making them inconvenient to carry around. This is a very serious problem for patients who must carry around their MDIs at all times for acute asthma attacks. Because they are so bulky, MDI users often leave their spacers at home instead of carrying it with them. Thus, there is a need for a spacer device that is compact and easy-to-carry, yet large enough for effective drug delivery.

SUMMARY

The present invention provides a compact spacer device for a metered dose inhaler. In one aspect, the present invention is a spacer device for a metered dose inhaler (MDI). The spacer device has a proximal end and a distal end. The proximal/distal designation follows the direction of medication flow from the MDI, through the aerosol chamber, and out to the user. The spacer device may be made as a single unitary structure, or its various segments may be separate parts that are joined together. The spacer device or parts thereof could be made using any suitable type of material, including plastic materials such as polyethylene-vinyl-acetate (PEVA), polyethylene, polypropylene, silicone, etc.

Aerosol Chamber:

The spacer device comprises an aerosol chamber for holding the aerosolized medication sprayed from the MDI. The aerosol chamber could be designed in any suitable way for this purpose. In some embodiments, the aerosol chamber comprises a forward shell, a rear shell, and an extendable barrel in between. For example, the extendable barrel may comprise a flexible plastic sheath that is supported by a coiled wire spring.

In another embodiment, the aerosol chamber comprises a main barrel in the shape of a corrugated tube, which allows the aerosol chamber to have a compressed configuration and an expanded configuration. The main barrel segment could have any suitable cross-sectional shape, such as circular, oblong, oval, rounded square or rectangle, etc. (which may be symmetrical or asymmetrical).

In some embodiments, the aerosol chamber further comprises a one-way valve that permits air flow coming out of the aerosol chamber into the mouthpiece (e.g. when the user inhales), but diverts air flow coming from the mouthpiece away from the interior of the aerosol chamber (e.g. when the user exhales into the spacer).

Mouthpiece:

At the distal end of the aerosol chamber, there is a mouthpiece. In some embodiments, the distal mouthpiece is in the shape of a corrugated tube, which allows the mouthpiece to have a compressed configuration and an expanded configuration. In some embodiments, the mouthpiece comprises a rigid segment at the distal end of the mouthpiece, wherein the rigid segment is more rigid than a more proximally-located segment of the mouthpiece. The spacer device may further comprises a mouthpiece cover that comprises a mouthpiece cap for fitting onto the mouthpiece.

Fastening Means:

The spacer device comprises a fastening means to couple the MDI to the spacer device. The fastening means may have any suitable design. In some embodiments, the fastening means is a mounting bracket to hold the MDI. The mounting bracket could have any suitable design to hold the MDI such that the mouthpiece of the MDI is aligned with the aerosol chamber of the spacer device. In one embodiment, the mounting bracket comprises flexing holder arms for gripping the actuator boot of the MDI. The MDI is held in the mounting bracket such that the mouthpiece of the MDI is mated with the aerosol chamber. In some cases, the mounting bracket has a support wall that is parallel and flush against the aerosol chamber.

Examples of other types of fastening means include anchoring knobs, through-holes for mating, elastic bands, pivoting rods, plastic ties, harnesses, latches, hooks, snaps, Velcro (hook-and-loop fastening), etc. In some embodiments, the fastening means couples the proximal end of the aerosol chamber or the adapter to the spray outlet of the MDI. For example, such a fastening means could be an elastic band. In another example, the collar described below could be considered a fastening means. The spacer device could comprise two or more fastening means.

In some embodiments, the spacer device comprises a second fastening means. In this embodiment, the first fastening means located at a proximal portion of the aerosol chamber. As used herein, the term "proximal portion" in relation to the aerosol chamber means the proximal one-fourth end section of the aerosol chamber. The second fastening means is located above (distal to) the first fastening means. In the embodiment where the spacer device comprises a mouthpiece cover, the mouthpiece cover could comprise the second fastening means for coupling to the MDI. In this design, the second fastening means could couple to the mounting bracket, or actuator boot, or the medication canister of the MDI. In this way, the mouthpiece cover of the spacer device is coupled to the mounting bracket, actuator boot, or the medication canister of the MDI. This coupling is detachable, that is, the mouthpiece may be uncoupled from the MDI so that the mouthpiece is accessible for use by the user.

Adapter:

The aerosol chamber may further comprise an adapter to enable the spacer device to adopt different configurations. The adapter has a hollow interior to give continuity between the MDI and the aerosol chamber. The mouthpiece of the MDI may be inserted into the adapter. Any of various types of adapter configurations could be used. Swivel Adapter: In some embodiments, the adapter is a swivel-type adapter. This type of adapter could have any suitable design. In one embodiment, the adapter comprises an outer case and an inner case, wherein the inner case is within the outer case. The inner case and the outer case are rotatably slidable relative to each other. The inner case and the outer case could be made of a hard plastic material.

Flexible Tube Adapter:

In some embodiments, the adapter is a flexible tube-type adapter. This type of adapter could be in the shape of a tube, which could have any suitable cross-sectional shape, such as circular, oblong, oval, rounded square or rectangle, etc. (which may be symmetrical or asymmetrical). In some embodiments, the adapter is in the shape of a corrugated tube. In this embodiment, the fastening means may be located on the adapter. In some embodiments, the adapter is made to be more flexible than the main barrel. In some embodiments, the adapter is made of a natural or synthetic rubber material, such as silicone rubber, latex rubber, styrene-butadiene rubber, butyl rubber, etc.

Collar:

The proximal end of the aerosol chamber is coupled to the spray outlet of the MDI. Any suitable design could be used for this purpose. In some embodiments, the adapter comprises a collar for receiving the mouthpiece of the MDI and help coupling of the MDI to the space device. The collar could be made of a soft material, such as silicone plastic, to promote a secure fit with the mouthpiece of the MDI. In some embodiments, the spacer device further comprises a cushion positioned against the support wall of the mounting bracket and between the MDI. The cushion mates with the adapter. The cushion may be made of a softer material than the mounting bracket, such as silicone plastic or polyurethane foam. In this embodiment, the cushion comprises the collar for receiving the mouthpiece of the MDI. In some cases, the cushion comprises an outwardly protruding bumper on the side facing towards the MDI. This bumper may be useful to dampen loose rattling of the MDI in the mounting bracket.

Dimensions:

There are a range of dimensions suitable for design of the spacer device and its various components. As an example, the full length of the aerosol chamber may be in the range of 3-18 or 3-9 cm in its compressed configuration and 9-22 or 9-30 cm in its expanded configuration. As an example, the length of the main barrel may be in the range of 3-7 cm or 3-9 cm in its compressed configuration, and 8-20 or 8-26 cm in its expanded configuration. As an example, the outer diameter of the main barrel may be in the range of 2-7 cm wide. As an example, the volume of the aerosol chamber in expanded configuration may be in the range 50-800 $cm^2$; and in some cases, at least 125 $cm^2$. In embodiments where the mouthpiece has a compressed/extended configuration, as an example, the length of the mouthpiece may be in the range of 1-3 cm in its compressed configuration and 2-6 cm in its extended configuration. As an example, the outer diameter of the mouthpiece may be in the range of 1-2.5 cm.

Medical Inhaler Assembly:

In another aspect, the present invention is a medical inhaler assembly. The assembly comprises a MDI and a spacer device of the present invention. The spacer device is coupled to the MDI such that the aerosol chamber or the main barrel of the aerosol chamber is aligned substantially parallel to the actuator boot of the MDI. This coupling may be detachable or permanent. The actuator boot of the MDI and the spacer device could be combined as a single unitary device (with the medication canister being replaceable). In some embodiments, the proximal end of the aerosol chamber or the adapter is coupled to the spray outlet of the MDI in the manner already described above. This coupling may be detachable or permanent.

Regardless of how the coupling between the spacer device and the MDI is done, the inhaler assembly is put into a compact configuration in which the aerosol chamber or the main barrel of the aerosol chamber is aligned substantially parallel to the actuator boot of the MDI. In some embodiments, the aerosol chamber is positioned flush to the MDI, i.e. the gap between the aerosol chamber of the spacer device and the actuator boot of the inhaler is less than 2 cm; and in some cases, less than 1 cm. In some embodiments, the main barrel of the aerosol chamber is positioned flush to the MDI, i.e. the gap between the main barrel of the aerosol chamber and the actuator boot of the inhaler is less than 2 cm; and in some cases, less than 1 cm.

Method of Combining:

In another aspect, the present invention is a method of combining a MDI with a spacer device. The method comprises having a MDI and a spacer device of the present invention. The spacer device is coupled to the MDI by the one or more fastening means as described above. In embodiments where the spacer device comprises a mounting bracket, the method comprises positioning the MDI on the mounting bracket. In embodiments where the coupling includes a second fastening means on a mouthpiece cover, the method comprises placing the mouthpiece cap on the mouthpiece of the spacer device, or attaching the second fastening means to the mounting bracket, or actuator boot, or the medication canister of the MDI.

The spacer device is coupled to the MDI such that the aerosol chamber or the main barrel of the aerosol chamber is aligned substantially parallel to the actuator boot of the MDI. In some embodiments, the aerosol chamber is positioned flush to the MDI, i.e. the gap between the aerosol chamber of the spacer device and the actuator boot of the inhaler is less than 2 cm; and in some cases, less than 1 cm. In some embodiments, the main barrel of the aerosol chamber is positioned flush to the MDI, i.e. the gap between the main barrel of the aerosol chamber and the actuator boot of the inhaler is less than 2 cm; and in some cases, less than 1 cm.

Method of Use:

In another aspect, the present invention is a method of using a MDI with a spacer device of the present invention. To prepare for use, the aerosol chamber is folded downward away from the MDI. As an example, the angle of folding could be in the range of 60-150° or 75-135°. In embodiments where the spacer device comprises a swivel adapter, this involves the step of swiveling the aerosol chamber downward. In embodiments where the spacer device comprises a second fastening means on a mouthpiece cover, this step involves removing the mouthpiece cap off the mouthpiece of the spacer device.

With the aerosol chamber folded downward into open position, the aerosol chamber is then expanded in a distal direction along its main longitudinal axis. In embodiments where the aerosol chamber comprises a forward shell, a rear shell, and an extendable barrel, this involves the step of separating the forward shell from the rear shell. The barrel may self-extend outward under spring action, or by the user pulling on the forward shell, or a combination of both. In embodiments where the mouthpiece of the spacer device comprises a rigid segment at its distal end, and the user grasps the rigid segment to pull the aerosol chamber and mouthpiece out in the distal direction.

The user may insert the mouthpiece of the spacer device into their mouth and actuate the MDI. In some embodiments, the method further comprises, after use, compressing the aerosol chamber back into its compressed configuration. The aerosol chamber is folded back upward to put the spacer device back into its compact configuration. In embodiments where the spacer device comprises a second fastening means on a mouthpiece cover, this step involves placing the mouthpiece cap back on the mouthpiece of the spacer device.

BRIEF DESCRIPTION OF THE DRAWINGS

FIG. 1 shows a perspective view of an example of a metered dose inhaler and its mechanism of action.

FIG. 2 shows a side view of an example of a conventional spacer device of the prior art.

FIGS. 3A and 3B show an example of a compact spacer device of the present invention;

FIG. 3A shows a perspective view; FIG. 3B shows a side view.

FIGS. 4A-4E show how the compact spacer is operated by the user. FIG. 4A shows the metered dose inhaler separate from the compact spacer. FIG. 4B shows how the user combines the inhaler with the compact spacer so that they are bundled together in a compact configuration. FIG. 4C shows that the cap is lifted off the mouthpiece of the spacer, thus releasing the mouthpiece end from its attachment to the inhaler. FIG. 4D shows the spacer in its extended configuration. FIG. 4E shows a cutaway view of the user's head with the mouthpiece segment inserted into the user's mouth.

FIG. 5 shows the various dimension parameters that may be selected for each segment of the spacer device.

FIGS. 6A-6C show an example of a compact spacer of the invention, drawn in schematic form to focus attention on the dimensions. FIG. 6A shows the spacer in its compressed configuration. FIG. 6B shows the outer diameter of the main barrel segment. FIG. 6C shows the spacer in its extended configuration.

FIGS. 7A-7C show an example of a compact spacer having a larger bore size for the main barrel segment. FIG. 7A shows the spacer in its compressed configuration. FIG. 7B shows the outer diameter of the main barrel segment. FIG. 7C shows the spacer in its extended configuration.

FIG. 8 shows an example of an inhaler assembly in which a spacer of the present invention is permanently attached to an inhaler.

FIGS. 9A-9C show another example of an inhaler assembly in which a spacer of the present invention is detachable or permanently attached to an inhaler. FIG. 9A shows the spacer and the inhaler as separate components. FIG. 9B shows the spacer being attached to the inhaler. FIG. 9C shows the spacer swiveled downward towards a straightened configuration.

FIGS. 10A and 10B show an example of an inhaler assembly in which a spacer of the present invention is detachably associated with an inhaler. FIG. 10A shows the spacer detached from the inhaler. FIG. 10B shows the spacer and the inhaler assembled together.

FIGS. 11A and 11B show perspective views of another example of a compact spacer device of the present invention.

FIGS. 12A and 12B show the compact spacer device with the aerosol chamber swiveled down in preparation for use.

FIG. 13 shows a rear perspective view of the spacer device with the inhaler omitted to show the interface between the two more clearly.

FIG. 14 shows a cut-away, perspective side view of the compact spacer device with the aerosol chamber swiveled down in preparation for use.

FIGS. 15A and 15B show the compact spacer device with the aerosol chamber in opened and extended configuration for use.

FIG. 16 shows the dimensions of the spacer device in its compact configuration.

FIG. 17 shows the dimensions of the spacer device in its fully extended configuration.

FIG. 18 shows the interior part of the aerosol chamber in isolation from the rest of the spacer device.

FIGS. 19A and 19B show parts of the spacer device in further isolation.

FIGS. 20A and 20B show the outer case and rear shell in two halves.

DETAILED DESCRIPTION

To assist in understanding the invention, reference is made to the accompanying drawings to show by way of illustration specific embodiments in which the invention may be practiced. The drawings herein are not necessarily made to scale or actual proportions. For example, lengths and widths of the components may be adjusted to accommodate the page size.

Figure 1:
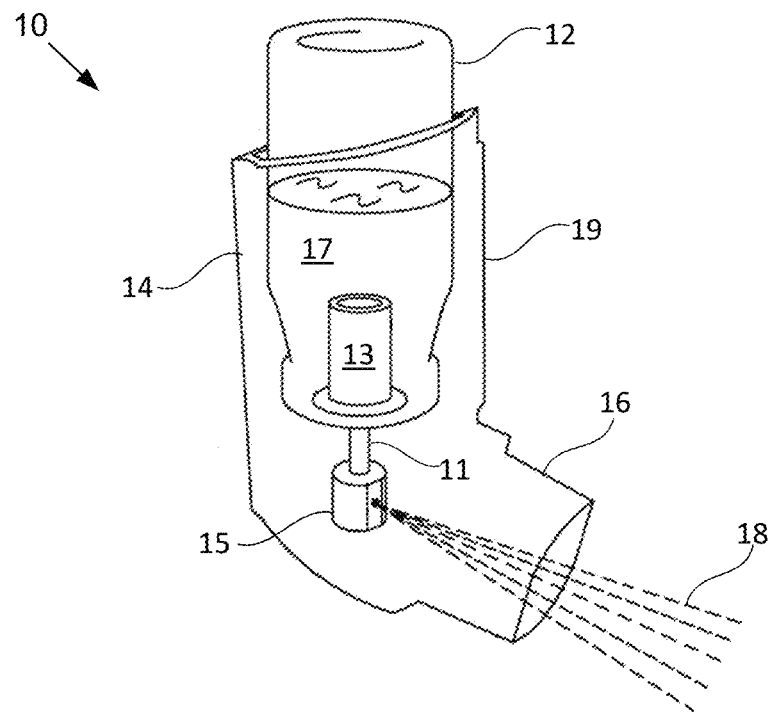
Figure 2:
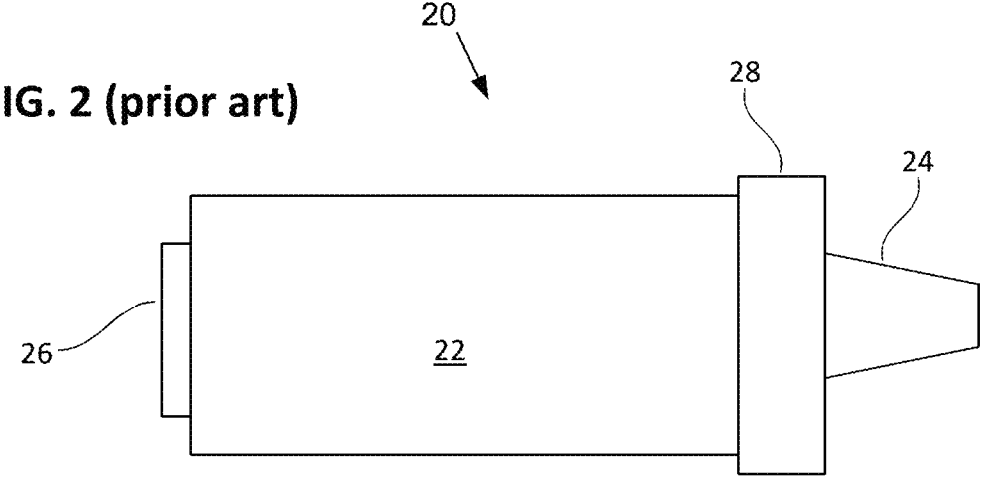
Figure 3A:
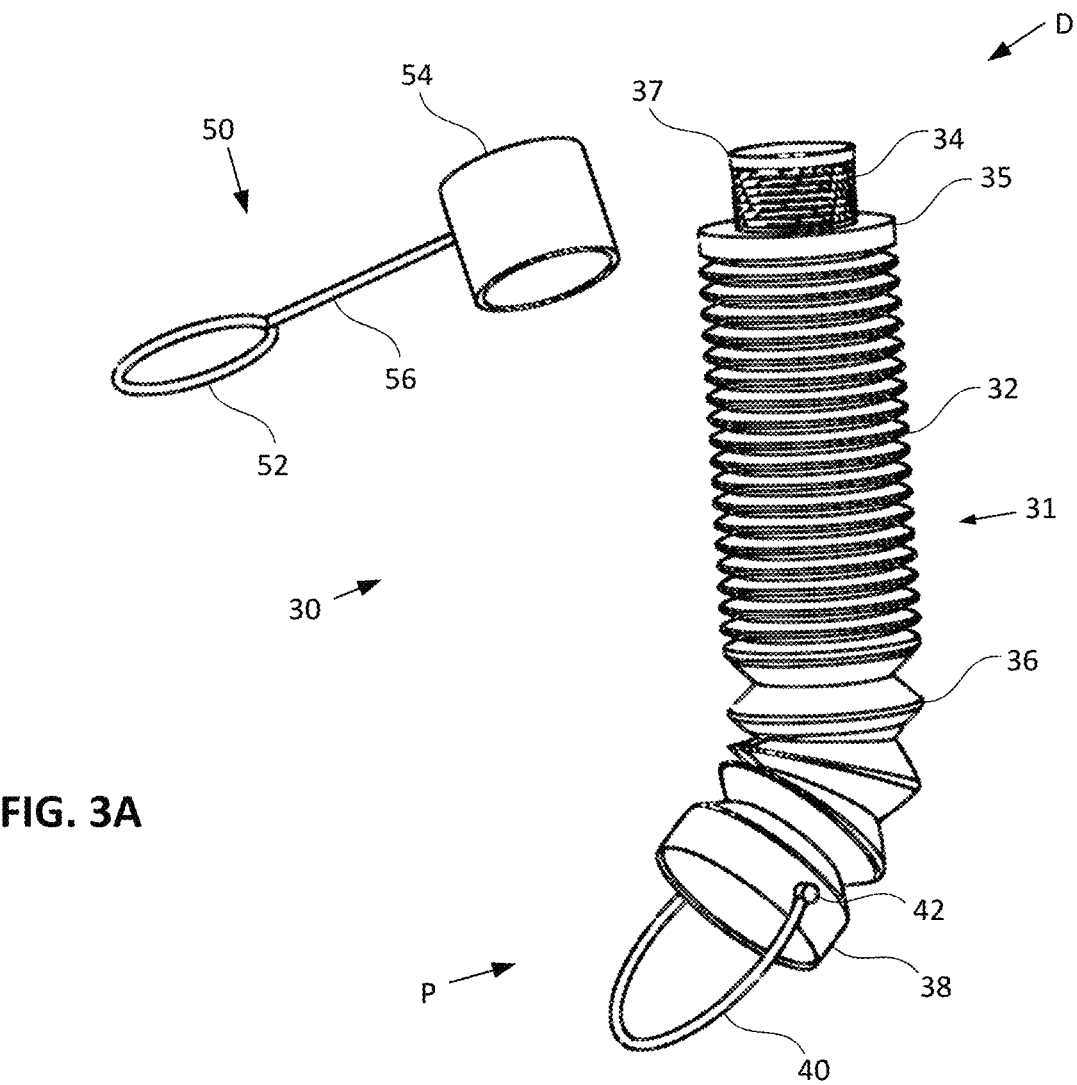
Figure 3B:
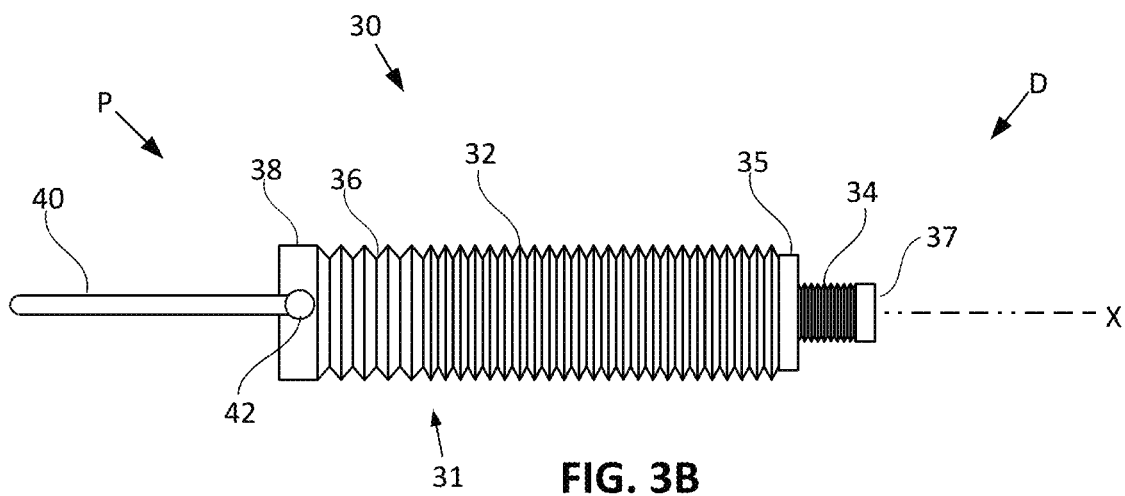

FIGS. 3A and 3B show an example of a compact spacer device 30 of the present invention; FIG. 3A shows a perspective view; FIG. 3B shows a side view. To specify orientation, the distal end is indicated by the reference label "D" and the proximal end is indicated by the reference label "P". The spacer 30 comprises an aerosol chamber 31 that holds the aerosolized medication from the inhaler. The aerosol chamber 31 comprises a adapter segment 36 and a main barrel segment 32. The main barrel segment 32 is made as a flexible corrugated tube that has folding pleats that allow the tube to be extended and compressed along its longitudinal axis "X". The folding pleats also allow the main barrel section 32 to be flexed. The main barrel segment 32 is made of an anti-static material or has an anti-static coating to avoid static interference with the aerosolized medication.

Proximal to the main barrel segment 32, there is a flexible adapter segment 36 that fits onto the mouthpiece of the inhaler. The adapter segment 36 is made as a pleated tube of silicone rubber with high flexibility. The hollow interior of the adapter segment 36 is continuous with that of the main barrel segment 32. A collar 38 on the adapter segment 36 is designed to fit snugly onto the mouthpiece of an inhaler. The functional purpose of the highly flexible adapter segment 36 is explained below with respect to FIGS. 4A-4E.

At the distal end of the aerosol chamber 31 is a flange 35 where the mouthpiece segment 34 connects. Mouthpiece segment 34 is also made as a corrugated tube. The mouthpiece segment 34 has a smaller diameter than the aerosol chamber 31. The distal tip of the mouthpiece segment 34 is a sturdy rim 37 for grasping when extending the mouthpiece segment outward. The sturdy rim 27 also helps to avoid flattening or crushing of the mouthpiece segment 34 when inside the user's mouth. The rim 37 could be made stiff by any suitable means, such as choice of harder materials, thicker wall, double wall, reinforcement (e.g. wire coils), or any other suitable manner.

Affixed to the adapter segment 36 is an elastic strap 40 for wrapping around the actuator 19 of the inhaler 10. Accompanying the spacer 30 as an accessory part is a mouthpiece cover 50, which comprises an elastic ring 52, leash 56, and a cap 54. The elastic ring 52 fits around the canister 12 of the inhaler 10 and the cap 54 fits over the mouthpiece 34 of spacer 30. There is further information below about the function of elastic strap 40 and mouthpiece cover 50.

Figure 4A:
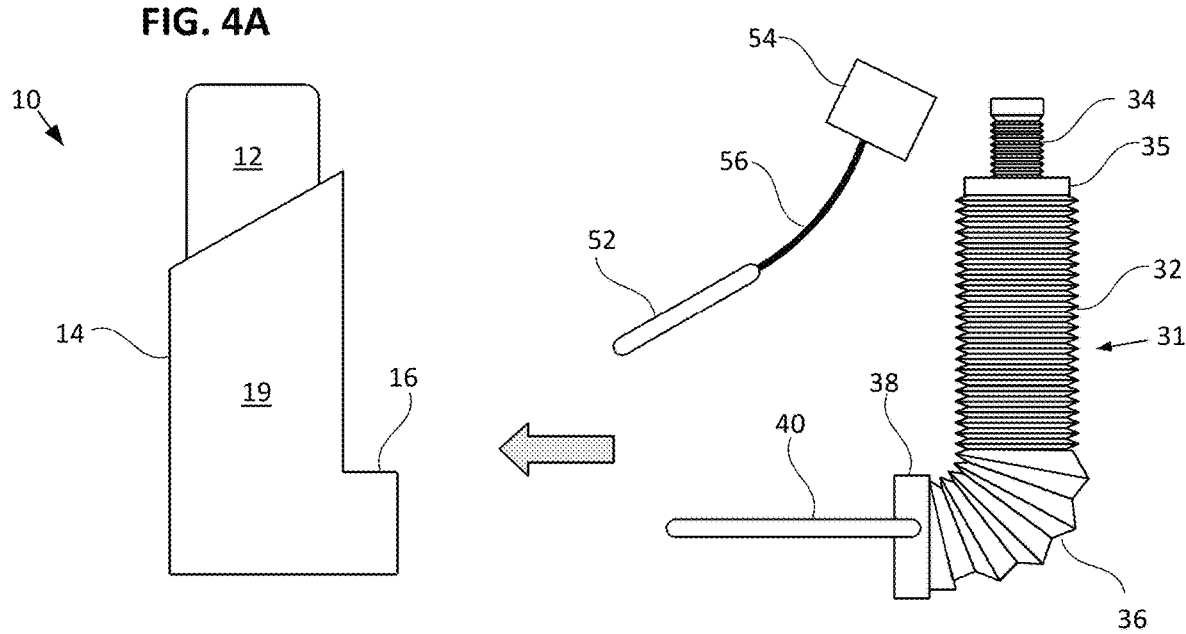
Figure 4B:
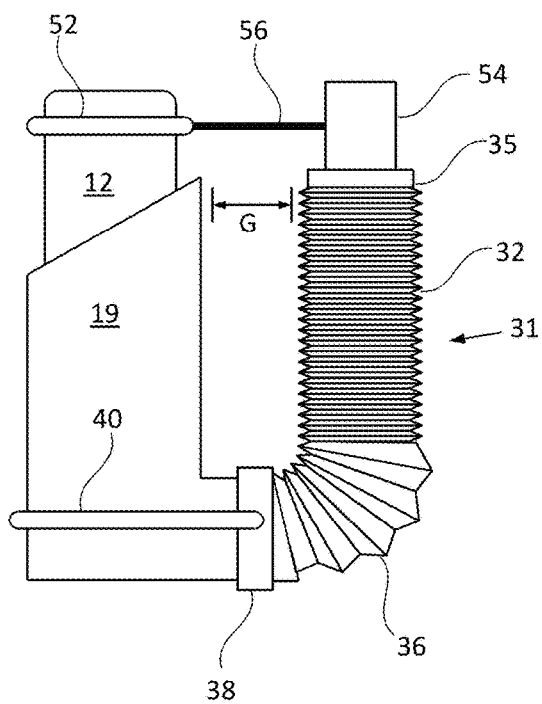

FIGS. 4A-4E show how the compact spacer 30 is operated by the user. FIG. 4A shows the metered dose inhaler 10 separate from the compact spacer 30. As shown in FIG. 4B, the user combines the inhaler 10 with the compact spacer 30 so that they are bundled together in a compact configuration. The collar 38 of the adapter segment 36 is fitted onto the mouthpiece 16 of the inhaler 10. This is secured by elastic strap 40 that is wrapped around the actuator 19 of the inhaler 10.

The mouthpiece cover 50 is used to secure the mouthpiece 34 end of the spacer 30 to the inhaler 10. The elastic ring 52 is encircled around the canister 12. At the other end, the cap 54 is seated onto the mouthpiece 34 of the spacer 30. With these attachments, the spacer 30 is held in a compact configuration alongside inhaler 10. The pleats on the main barrel segment 32 and mouthpiece 34 are compressed to minimize the length of spacer 30. The adapter segment 36 is made to bend so that the main barrel segment 32 is aligned parallel and flush to the actuator 19. The gap "G" separating the main barrel segment 32 from the actuator 19 is about 0.2 cm.

Figure 4C:
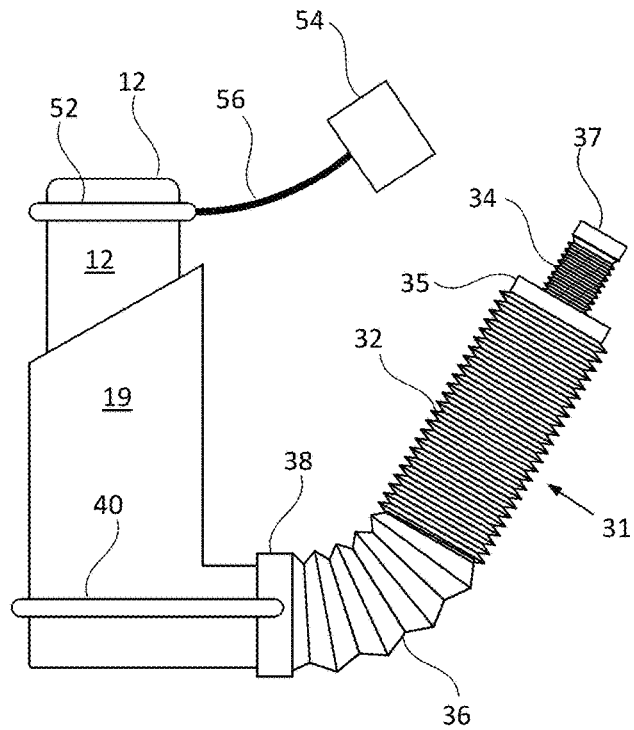
Figure 4D:
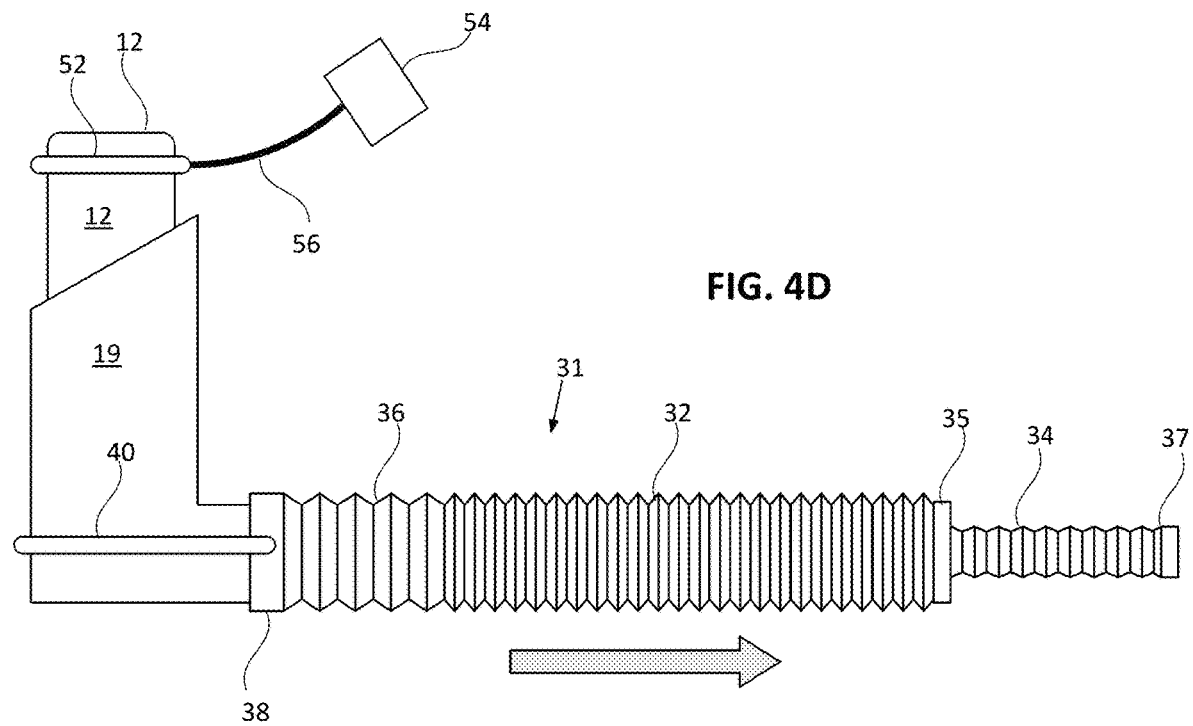
Figure 4E:
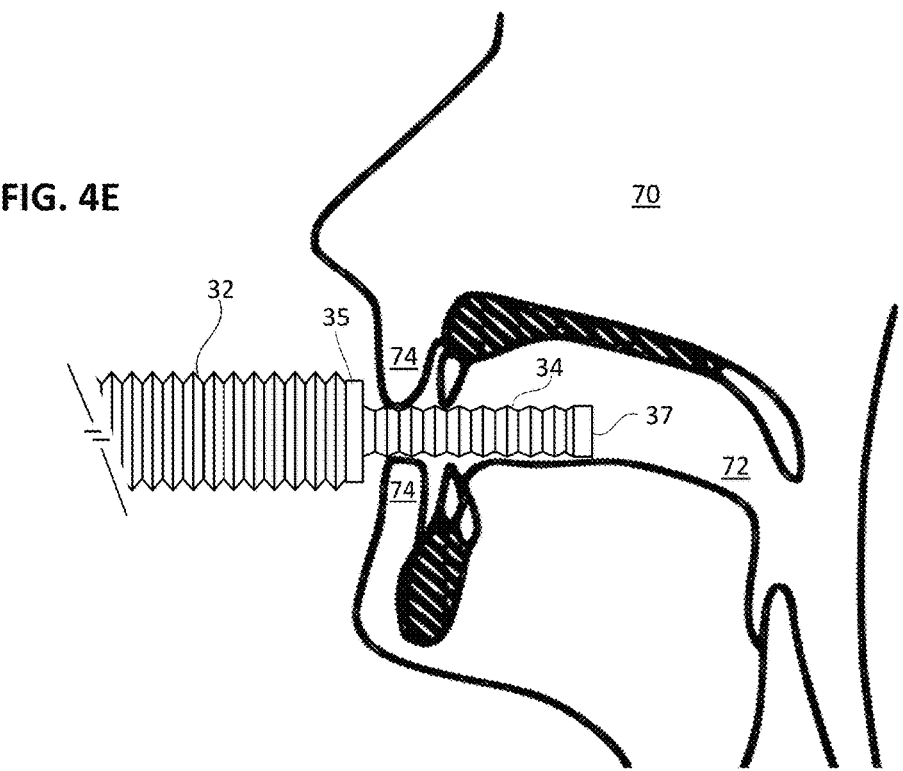

As shown in FIG. 4C, when the user wishes to use the inhaler 10, the cap 54 is lifted off the mouthpiece 34 of the spacer 30, thus releasing the mouthpiece 34 end from its attachment to the inhaler 10. As allowed by the highly flexible adapter segment 36, the main barrel segment 32 is pulled downward towards a straightened configuration. As shown in FIG. 4D, the user pulls out the main barrel segment 32 and mouthpiece segment 34 to extend the spacer 30 in a longitudinal direction. This expands the volume inside the spacer 30. FIG. 4E shows a cutaway view of the user's head 70 with the mouthpiece segment 34 inserted into the user's mouth for inhaling the aerosolized medication. Because mouthpiece segment 34 has a smaller diameter than the main barrel segment 32, the user can easily place their lips 74 abutting against the flange 35 on main barrel segment 32.

The narrow and extended length design of mouthpiece segment 34 adds flow resistance inside the hollow channel, thus slowing the inhalation flow rate. This helps to improve drug delivery to the lungs. Also, by reaching further into the user's mouth, the extended length design of mouthpiece segment 34 brings the distal end closer to the lungs, thereby improving the efficiency of drug delivery into the lung and reducing the deposition of aerosolized particles on the oropharynx 72 and upper airways.

Figure 5:
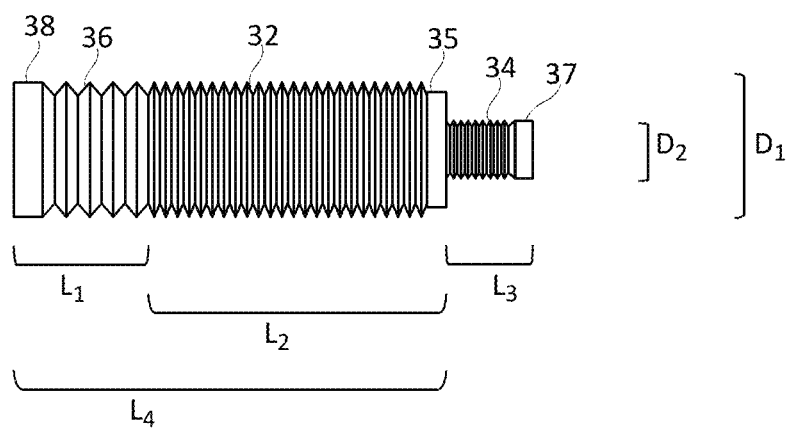

There are a range of dimensions suitable for design of the spacer and its various segments. FIG. 5 shows the various dimension parameters that may be selected for each segment of the spacer device. $L_1$ represents the length of the adapter segment 36. $L_2$ represents the length of the main barrel segment 32. $L_3$ represents the length of the mouthpiece segment 34. $L_4$ represents the length of the aerosol chamber as a whole. $D_1$ represents the outer diameter of the main barrel segment 32. $D_2$ represents the outer diameter of the mouthpiece segment 34. Possible numeric ranges for the dimensions are given in the "Summary" section above. The following illustrations show specific examples of dimensions that could be used.

Figure 6A:
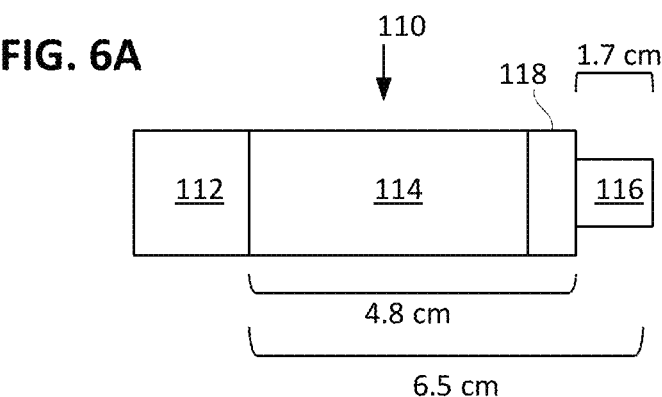
Figure 6B:
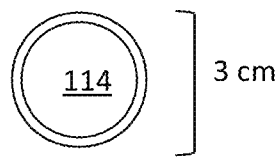
Figure 6C:
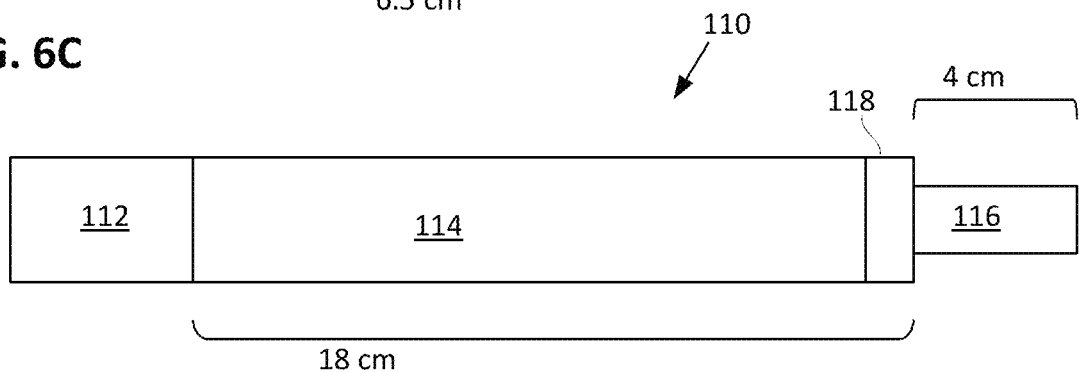

FIGS. 6A-6C show an example of a compact spacer 110 of the invention, drawn in schematic form to focus attention on the dimensions. The spacer 110 comprises an aerosol chamber comprised of an adapter segment 112 and a main barrel segment 114. The spacer 110 further comprises a mouthpiece segment 116. The main barrel segment 114 includes a one-way valve 118. FIG. 6A shows the spacer 110 in its compressed configuration. Here, the length of the main barrel segment 114 is about 4.8 cm. The length of the mouthpiece segment 116 is about 1.7 cm. The combined length of the main barrel segment 114 and the mouthpiece segment 116 is about 6.5 cm. As shown in FIG. 6B, the outer diameter of the main barrel segment 114 is about 3 cm. As shown in FIG. 6C, when the spacer 110 is extended for use, main barrel segment 114 lengthens to about 18 cm and the mouthpiece segment 116 lengthens to about 4 cm.

FIGS. 7A-7C show an example of a compact spacer 120 having a larger bore size for the main barrel segment 124.

The spacer 120 comprises an aerosol chamber comprised of an adapter segment 122 and the main barrel segment 124. The main barrel segment 124 includes a one-way valve 128. The spacer 120 further comprises a mouthpiece segment 126. As shown in FIG. 7A, in its compressed configuration, the main barrel segment 124 has a length of about 4 cm and the mouthpiece segment 126 has a length of about 1.7 cm. As shown in FIG. 7B, the larger-bore main barrel segment 124 has an outer diameter of about 5 cm. As shown in FIG. 7C, when the spacer 120 is extended for use, the main barrel segment 124 lengthens to 15 cm and the mouthpiece segment 126 lengthens to about 4 cm.

The spacer and the metered dose inhaler may be provided in combination as an assembly, with the spacer as either a detachable component or a permanent attachment. FIG. 8 shows an example of an inhaler assembly in which a spacer 82 of the present invention is permanently attached to an inhaler 80. The collar 84 on the adapter segment 86 is permanently attached to the spray outlet 88 of the inhaler 80. A flexible tether 83 is permanently affixed to the inhaler 80. The tether 83 holds a mouthpiece cap 85 that fits over the mouthpiece of the spacer 82. The assembly is configured such that the main barrel segment of the spacer 82 is aligned parallel and flush to the actuator body of inhaler 80.

Figure 9A:
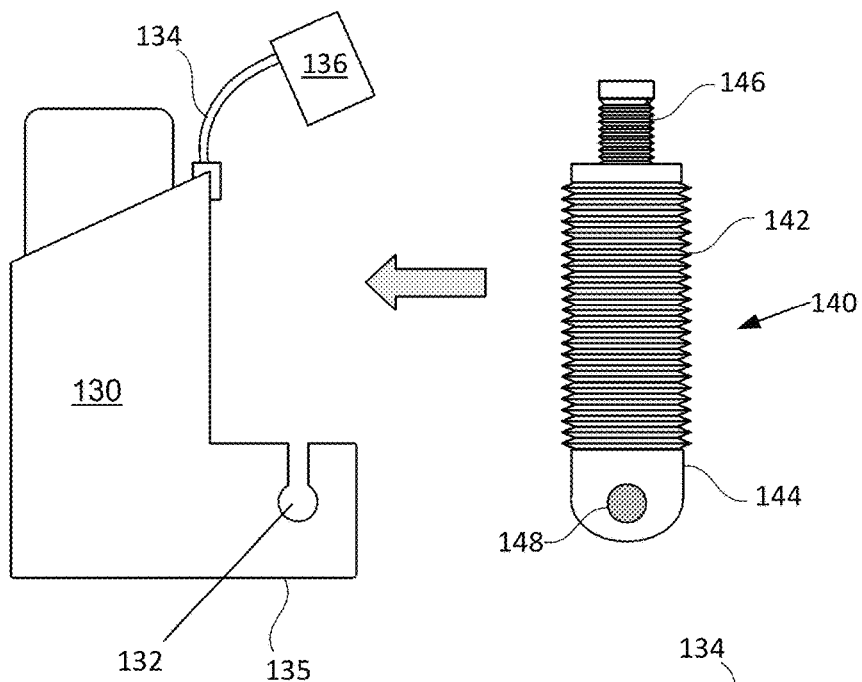
Figure 9B:
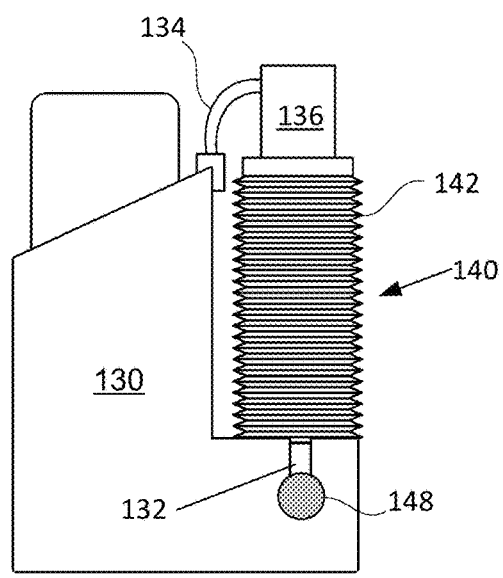
Figure 9C:
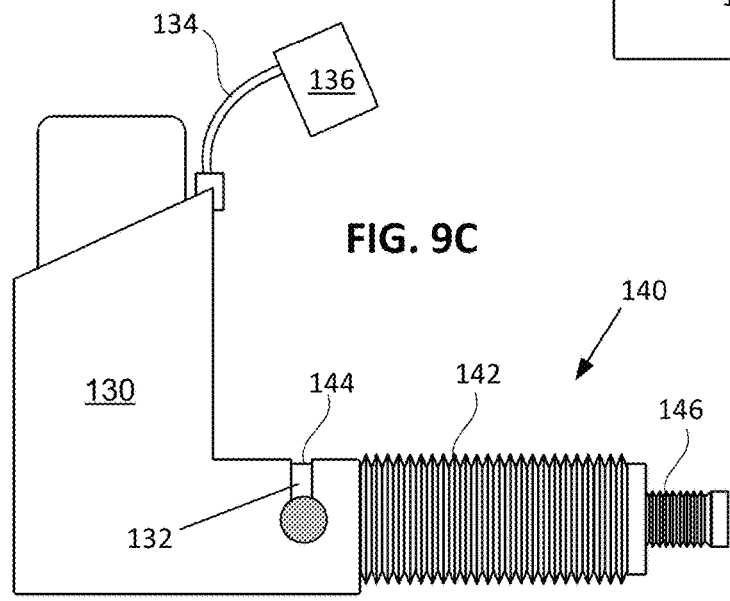

FIGS. 9A-9C show an example of an inhaler assembly in which a spacer 140 of the present invention is detachably, or alternately permanently, attached to an inhaler 130. FIG. 9A shows the spacer 140 and the inhaler 130 as separate components. The inhaler 130 has a spray outlet 135, which functions as a socket for receiving the spacer 140. A flexible tether 134 is permanently affixed to the inhaler 130. The tether 134 holds a mouthpiece cap 136 that fits over the mouthpiece 146 of the spacer 140. At the proximal end of the spacer 140, there is a socket adapter 144, which has a round bottom shape to make a seal inside the outlet 135 of the inhaler 130. The socket adapter 144 on spacer 140 has a swivel post 148.

As seen in FIG. 9B, the swivel post 148 slides down into the receiving slot 132 on the outlet 135 of inhaler 130. The mouthpiece cap 136 is fitted onto the mouthpiece 146 of the spacer 140. Thus, the inhaler assembly is configured such that the main barrel segment 142 of spacer 140 is aligned parallel and flush to the actuator body of inhaler 130.

As shown in FIG. 9C, when the user wishes to use the inhaler assembly, the cap 136 is lifted off the mouthpiece 146 of spacer 140, thus releasing the mouthpiece 146 end from its attachment to the inhaler 130. As allowed by the swivel engagement of socket adapter 144 to the outlet 135, the main barrel segment 142 is swiveled downward towards a straightened configuration. The user would then pull out the main barrel segment 142 and mouthpiece segment 146 to extend the spacer 140 in a longitudinal direction.

Figure 10A:
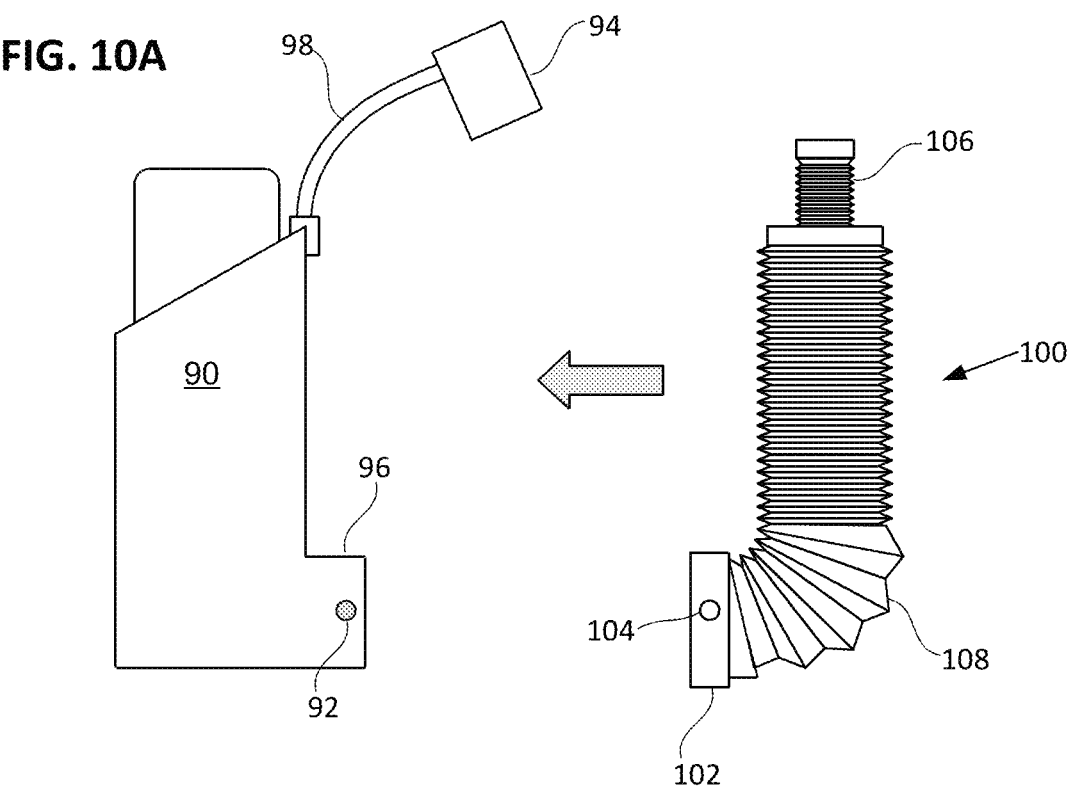
Figure 10B:
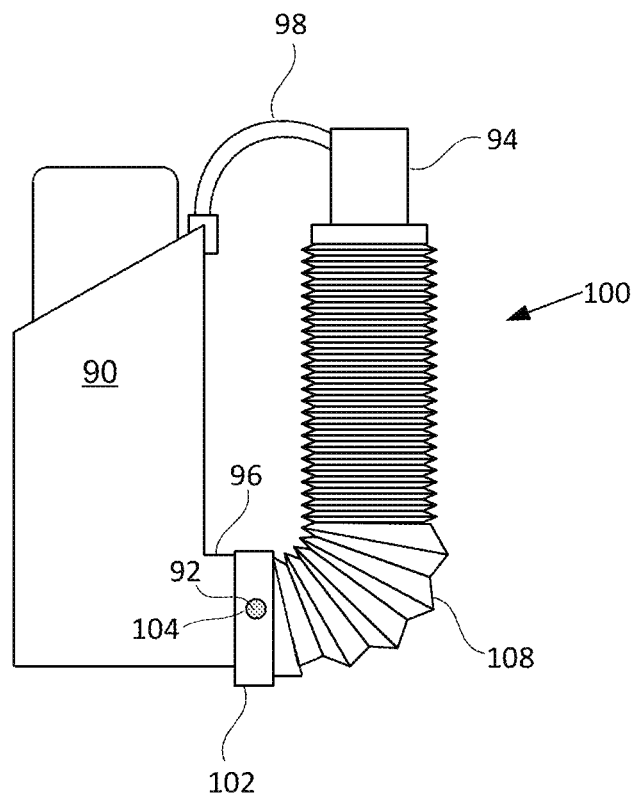

FIGS. 10A and 10B show an example of an inhaler assembly in which a spacer 100 of the present invention is detachably associated with an inhaler 90. FIG. 10A shows the spacer 100 detached from the inhaler 90. On the shell of the mouthpiece/outlet 96 of the inhaler 90 is a small protruding anchor 92. On the collar 102 of the adapter segment 108, there is a hole 104 for catching on anchor 92. The inhaler 90 also has a mouthpiece cap 94 that is attached to the body of inhaler 90 by a flexible tether 98. As shown in FIG. 10B, for assembling together, the collar 102 of the spacer 100 is snapped onto the mouthpiece/outlet 96 of the inhaler 90 via anchor 92 and hole 104. The tether 98 is flexed back slightly to accommodate the mouthpiece 106 of spacer 100. The mouthpiece cap 94 is then fastened onto the mouthpiece 106 of the spacer 100. The assembly is configured such that the main barrel segment of the spacer 100 is aligned parallel and flush to the actuator body of inhaler 90. Having the spacer 100 be detachable allows for easy cleaning of the spacer 100, as well as cleaning of the spray nozzle inside the inhaler 90.

Figure 11A:
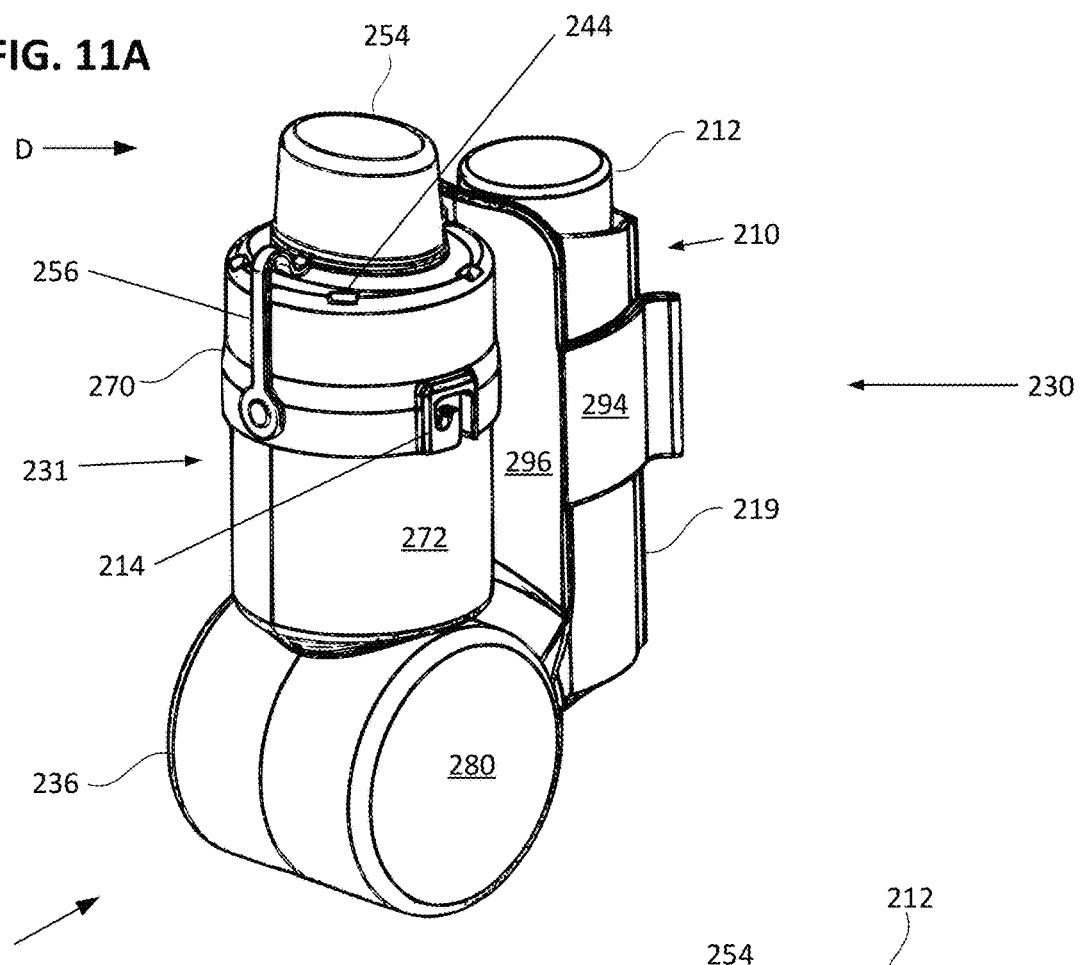
Figure 11B:
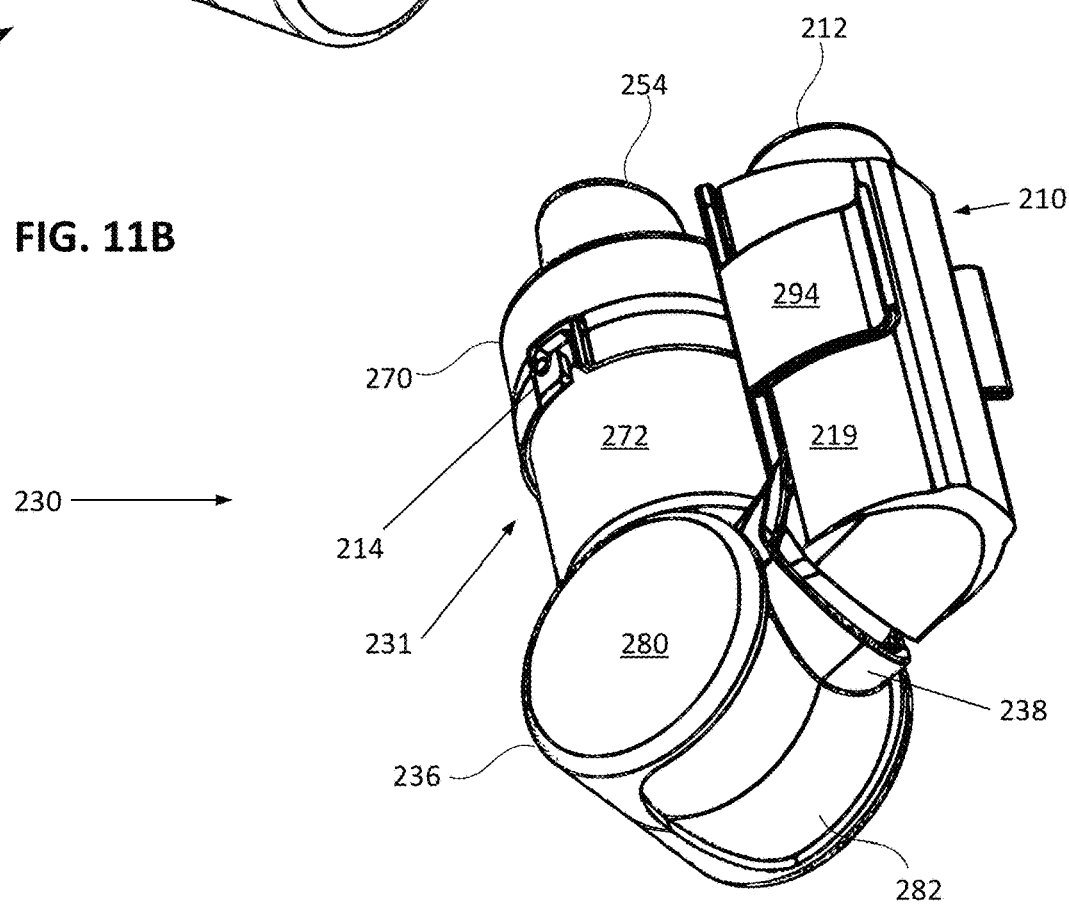

FIGS. 11A and 11B show perspective views of another example of a compact spacer device 230 of the present invention. FIG. 11A shows a side perspective view; FIG. 11B shows an underside perspective view. The spacer 230 comprises an aerosol chamber 231 that holds the aerosolized medication from the inhaler 210. The aerosol chamber 231 comprises a swivel adapter 236. The aerosol chamber 231 further comprises a forward shell 270 and a rear shell 272. In the compact configuration for the spacer device 230, the forward shell 270 and rear shell 272 are locked together via a twist lock 214. To specify orientation, the distal end is indicated by the reference label "D" and the proximal end is indicated by the reference label "P". This orientation follows the direction of medication flow from the metered dose inhaler 210, through the aerosol chamber 231, through the mouthpiece (not shown) of the spacer device 230, and out to the patient.

The inhaler 210 comprises a medication canister 212 held within an actuator body 219. The spacer device 230 further comprises a mounting bracket 296 and holder arms 294. The inhaler 210 is mounted onto the mounting bracket 296 and gripped in place by flexing holder arms 294. As seen in FIG. 11B, the swivel adapter 236 comprises an outer case 280 and an inner case 282 that are rotatably sliding relative to each other. Both the outer case 280 and the inner case 282 are made of hard plastic. On the inner case 282 of the swivel adapter 236, there is a collar 238 designed to receive the mouthpiece (hidden from view) of the inhaler 210. The collar 238 is made of soft silicone plastic to promote a snug fit around the mouthpiece of inhaler 210. The assembly is configured such that the aerosol chamber 231 of the spacer device 230 is aligned parallel to the actuator body 219 of inhaler 210.

A leash 256 is affixed to the forward shell 270 of the aerosol chamber 231. (Alternatively, the leash 256 could be affixed to mounting bracket 296.) The leash 256 holds the mouthpiece cap 254 that fits over the mouthpiece (not shown) of the spacer device 230. At the distal end of the aerosol chamber 231 is a mouthpiece (not shown) that is covered by a mouthpiece cap 254. Referring back to FIG. 11A, the forward shell 270 also has a series of vent holes 244 to allow air to expel if the user exhales into the spacer device 230 before inhaling. Inside the forward shell 270, there is a one-way valve 240 (see FIG. 17) that diverts the exhaled breath through the vent holes 244.

Figure 12A:
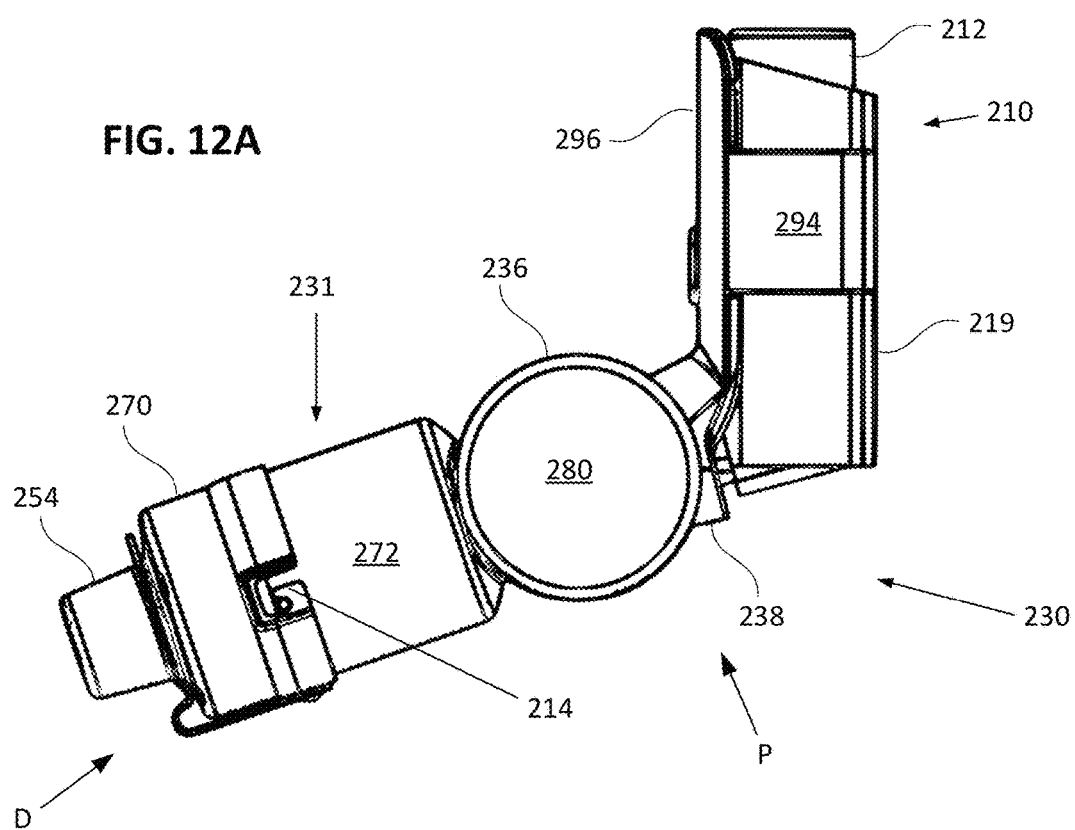
Figure 12B:
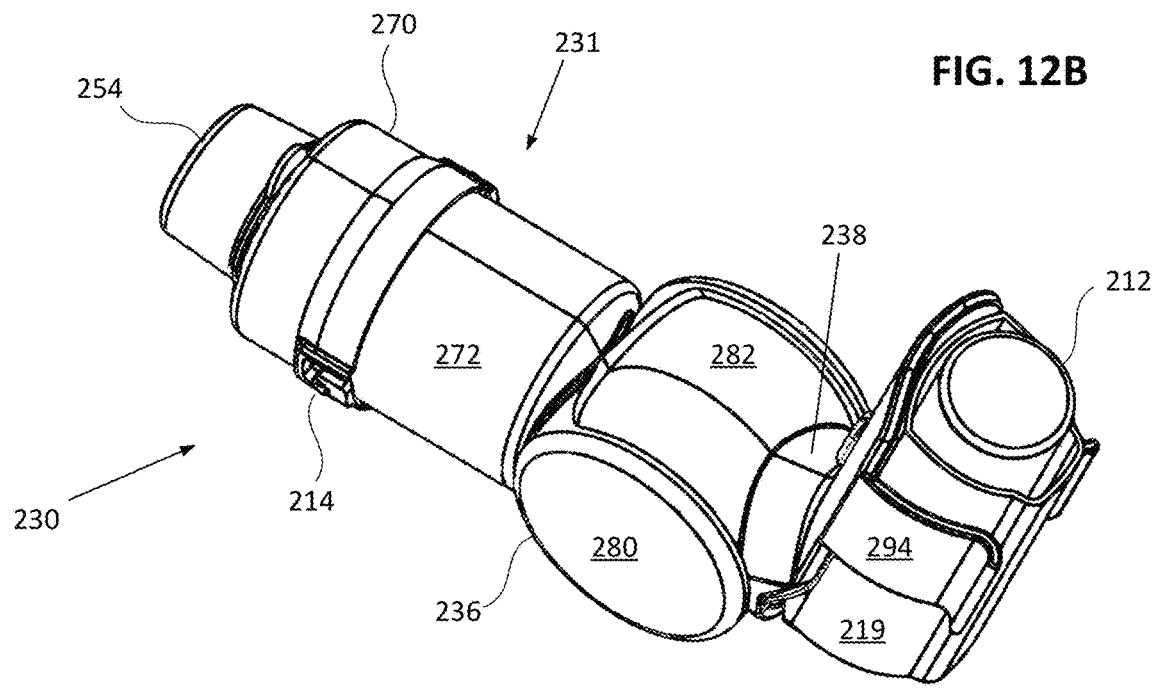

FIGS. 12A and 12B show the compact spacer device 230 with the aerosol chamber 231 swiveled down in preparation for use. FIG. 12A shows a side view; FIG. 12B shows a top perspective view. In this swiveled configuration, the outer case 280 of the swivel adapter 236 rotates around inner case 282 to give the swiveling motion.

FIG. 13 shows a rear perspective view of the spacer device 230 with the inhaler 210 omitted to show the interface between the two more clearly. This view again shows the collar 238 on the swivel adapter 236 that is designed to fit around the mouthpiece of the inhaler 210. Also seen is the opening 288 for receiving the aerosolized medication from the inhaler 210 into the aerosol chamber 231. The mounting bracket 296 comprises a support wall 298. In the compact configuration for spacer device 230, the support wall 298 is parallel and flush against the aerosol chamber 231.

FIG. 14 shows a cut-away, perspective side view of the compact spacer device 230 with the aerosol chamber 231 swiveled down in preparation for use. As seen in this view, the mouthpiece 237 of the inhaler 210 fits into the collar 238 of the swivel adapter 236. This view also shows the inside of aerosol chamber 231. In addition to the forward shell 270 and rear shell 272, there is an extendable barrel 232 in between. The extendable barrel 232 contains a coiled wire spring 260 that is shown in its collapsed configuration. Note that this version of the invention has a fin on the one-way valve 266, but that is not a necessary element.

Figure 15A:
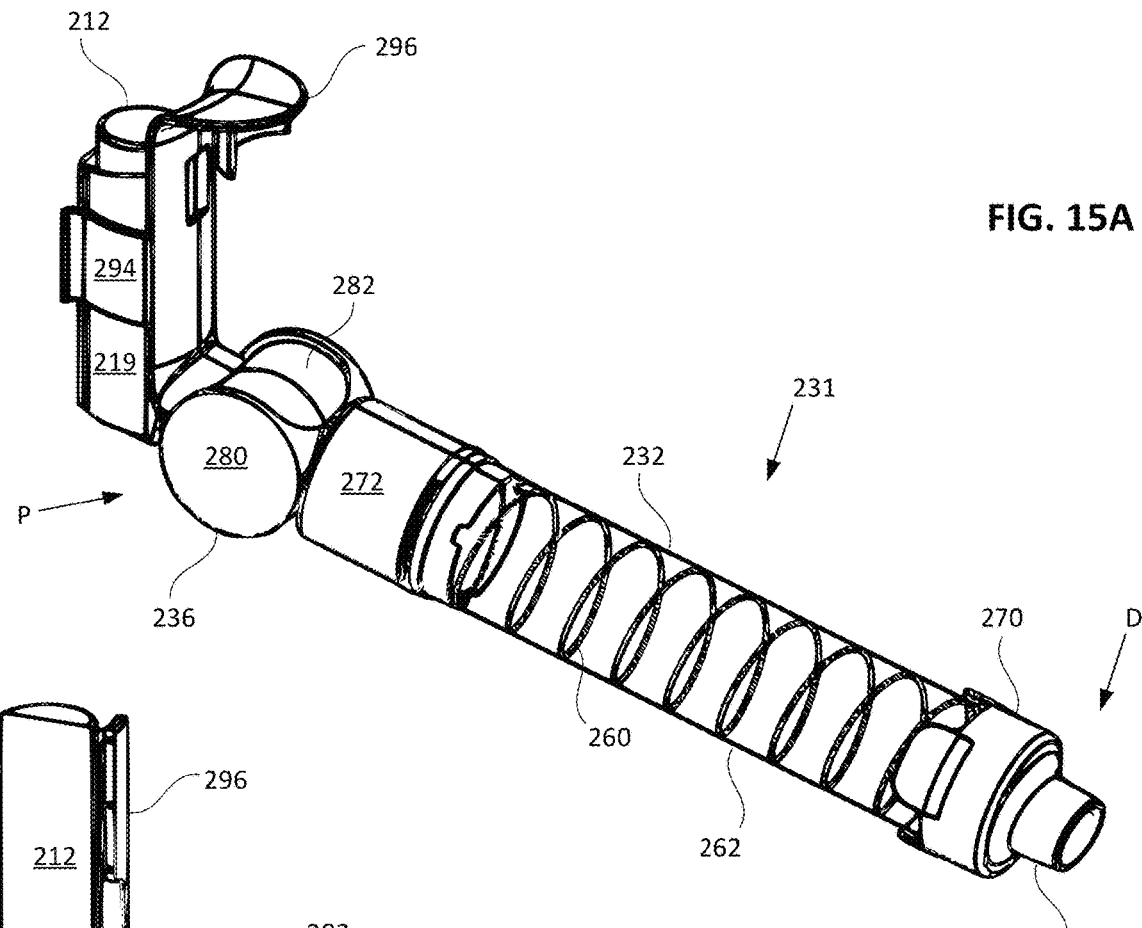
Figure 15B:
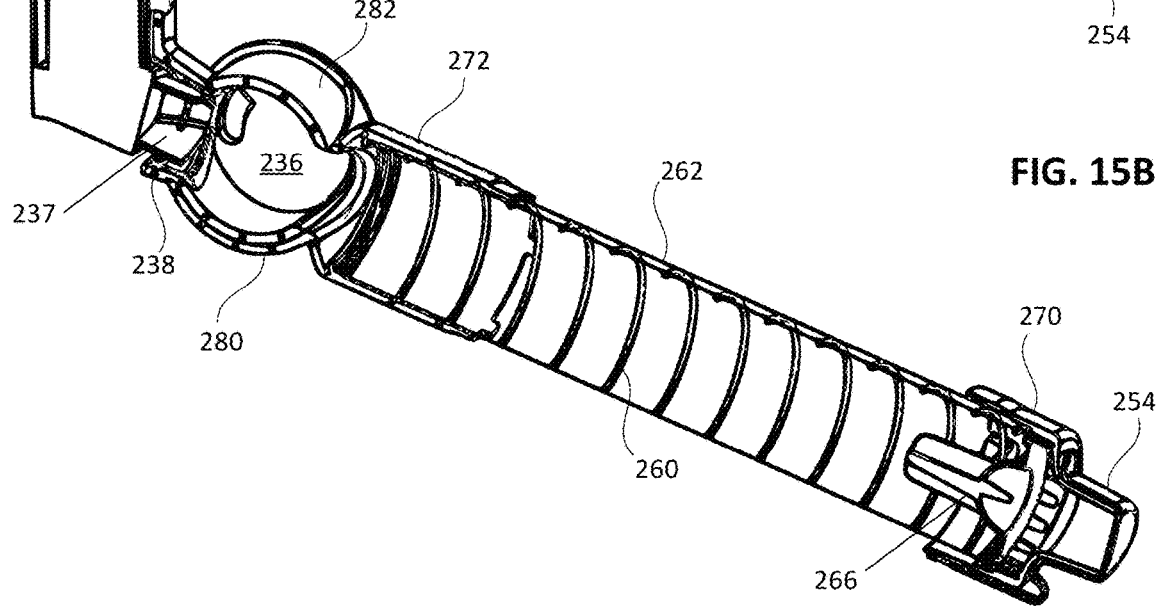

FIGS. 15A and 15B show the compact spacer device 230 with the aerosol chamber 231 in swiveled open and extended configuration for use. FIG. 15A shows a perspective view; FIG. 15B shows a cut-away view. Note that this version of the spacer device 230 has mating latches instead of a twist-lock. But referring to the other version, the aerosol chamber 231 is opened by untwisting the twist lock 214 and separating the forward shell 270 from the rear shell 272. The aerosol chamber 231 comprises an extendable barrel 232, which comprises a flexible plastic sheath 262 supported by a coiled wire spring 260 that serves as a framework. The sheath 262 is made of a soft plastic such as polyurethane. The forward shell 270 is pushed outward by the spring 260 to extend the barrel 232.

The cut-away view of FIG. 15B shows the interior parts of the spacer device 230. The swivel adapter 236 encloses a hollow cavity. The hollow interior of the extendable barrel 232 is continuous with the cavity of the swivel segment 236. This view also shows the one-way valve 266 at the mouthpiece end of the aerosol chamber 231. Note that this version of the spacer device 230 has a fin on the one-way valve 266, but that is not a necessary element. After use, the extendable barrel 232 is pushed back to make it collapse and allow it to mate with the rear shell 272. The rear shell 272 and forward shell 270 are push against each other to latch them together.

Figure 16:
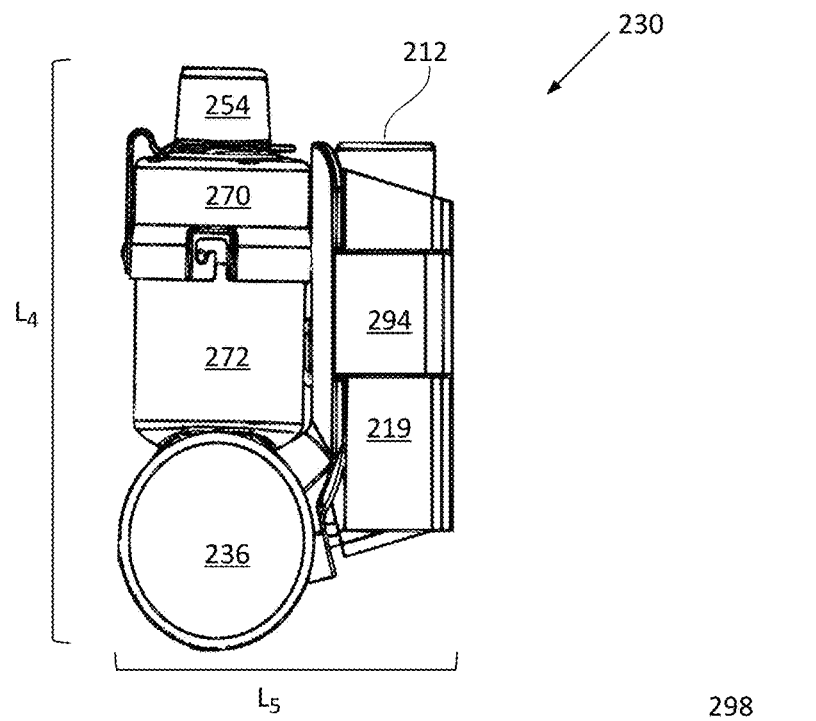

FIG. 16 shows the dimensions of the spacer device 230 in its compact configuration. Length $L_4$ is the length from the swivel adapter 236, across the aerosol chamber 231 (comprising shells 272 and 270), and to the end of the mouthpiece (hidden from view) under cap 254. In this particular example, length $L_4$ is about 11.7 cm. Length $L_5$ is the width from the front face of the spacer device 230 (along the edge of swivel adapter 236 and aerosol chamber 231) to the back face (along the edge of the actuator body 219 and the flexing holder arms 294). In this particular example, length $L_5$ is about 7.5 cm.

Figure 17:
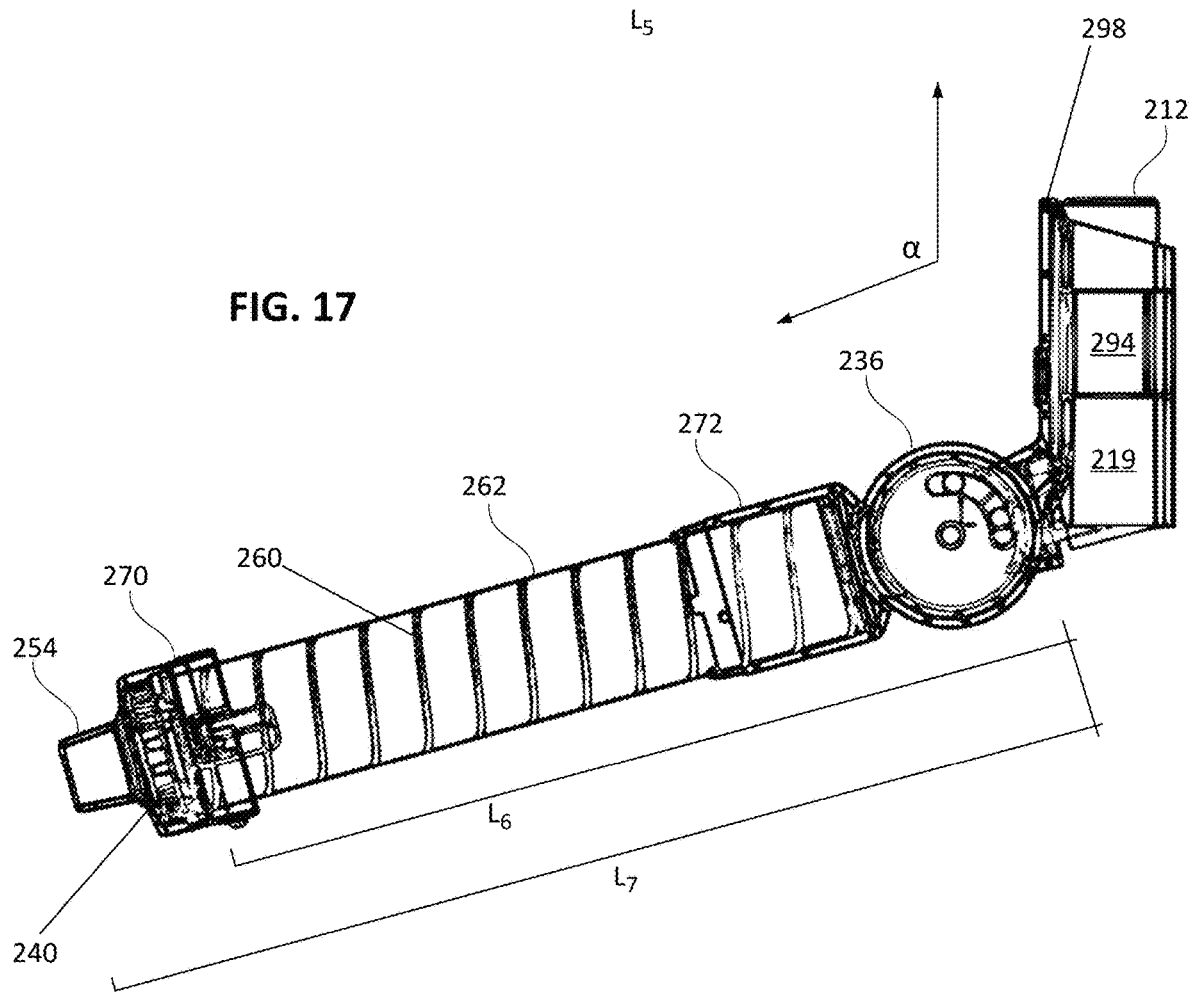

FIG. 17 shows the dimensions of the spacer device 230 in its fully extended configuration. Length $L_6$ represents the interior volume from the tip of the metered dose inhaler mouthpiece to the one-way valve 240 (see FIG. 18). In this particular example, length $L_6$ is about 20.8 cm. Length $L_7$ represents the overall length from the tip of the metered dose inhaler mouthpiece to the end of the mouthpiece on the distal end of the spacer device 230. In this particular example, length $L_7$ is about 23.3 cm. The angle α is the angle between the metered dose inhaler 210 or support wall 298 of the mounting bracket relative to the longitudinal axis of the extended aerosol chamber 231.

Figure 18:
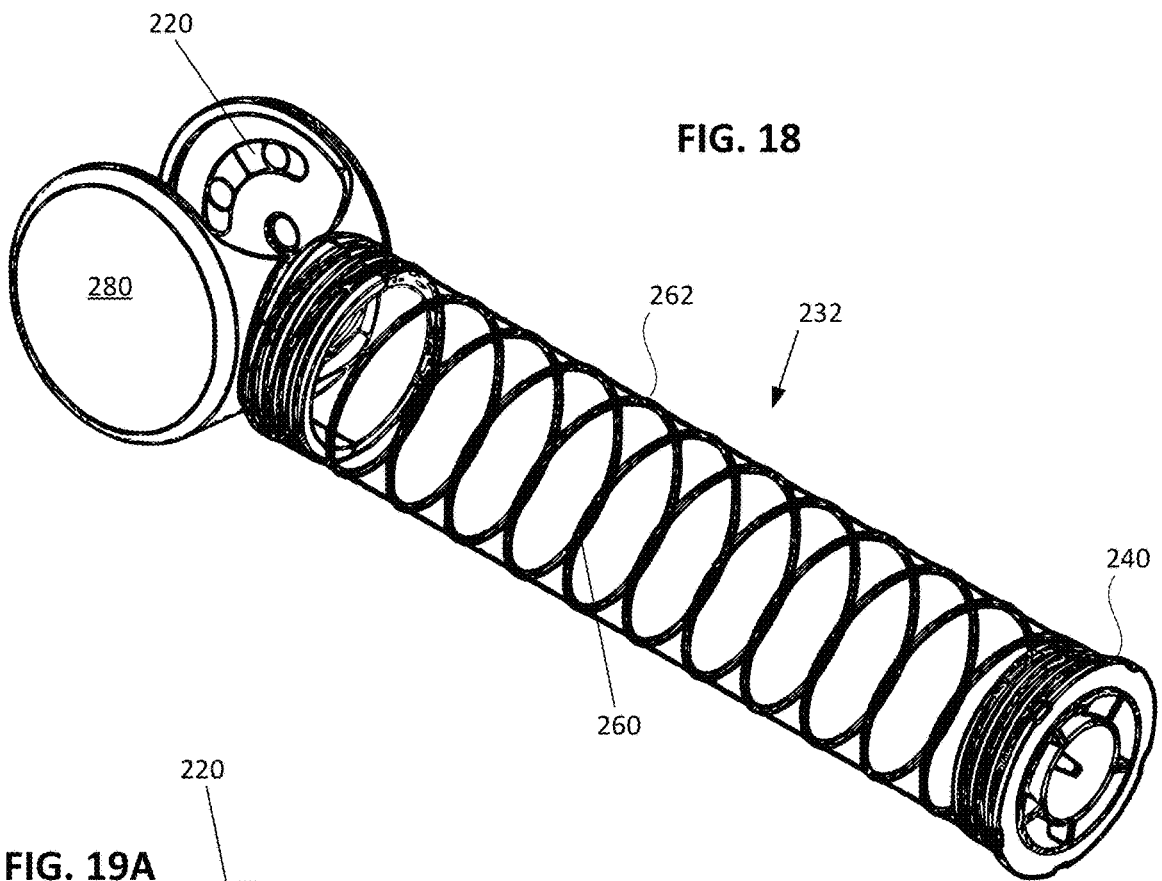

FIG. 18 shows the interior part of the aerosol chamber 231 in isolation from the rest of the spacer device 230. Shown here is the outer case 280 of the swivel adapter 236. On the inside surface of the outer case 280, there is a pivot groove 220 having two detents that help to retain the swivel adapter 236 in the folded-up or folded-down configuration. The interaction of the pivot groove 220 and the two detents are explained in reference to FIGS. 21A and 21B below. Also shown is the one-way valve 240 at the distal end of the extendable barrel 232.

Figure 19A:
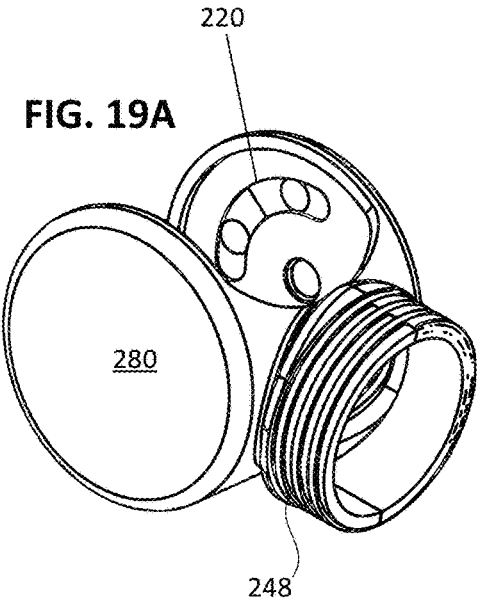
Figure 19B:
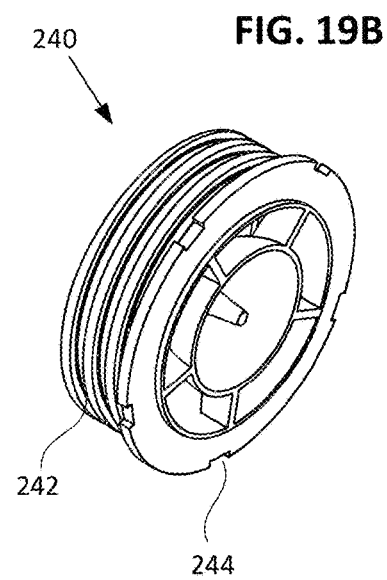

FIGS. 19A and 19B show parts of the spacer device 230 in further isolation. FIG. 19A shows the outer case 280; FIG. 19B shows the one-way valve 240. As shown in FIG. 19A, the outer case 280 has circular grooves 248 which engage with and hold the coiled wire spring 260 at its rear end. As shown in FIG. 19B, the one-way valve 240 also has circular grooves 242 that engage with and hold the coiled wire spring 260 at its forward end.

Figure 20A:
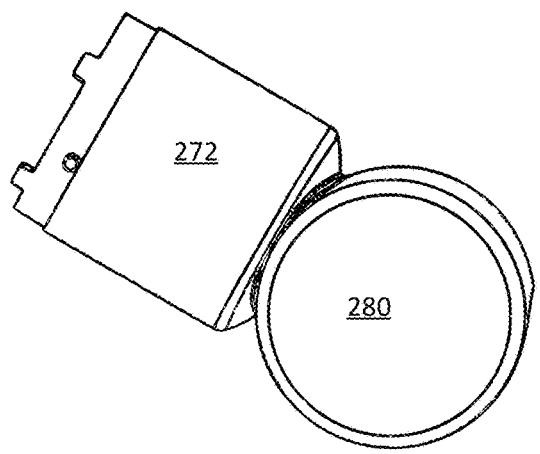
Figure 20B:
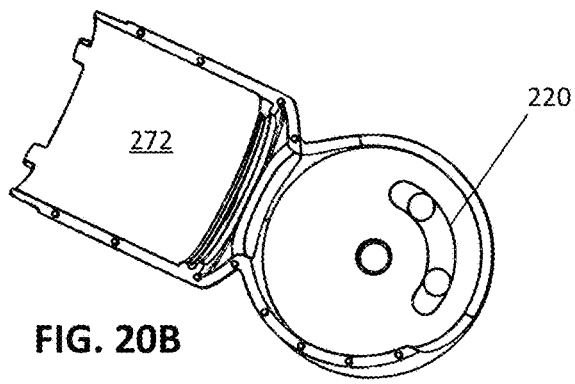

FIGS. 20A and 20B show the outer case 280 and rear shell 272 in two halves. FIG. 20A shows an exterior view; FIG. 20B shows an interior view. As seen in FIG. 20B, the interior surface of the outer case 280 has a pivot groove 220 with two detents (shallow depressions).

Figure 21A:
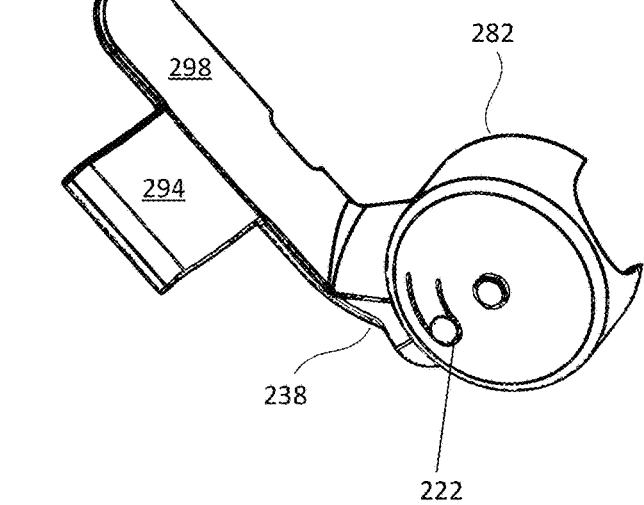
FIGS. 21A and 21B show the inner case and the mounting bracket in two halves.
Figure 21B:
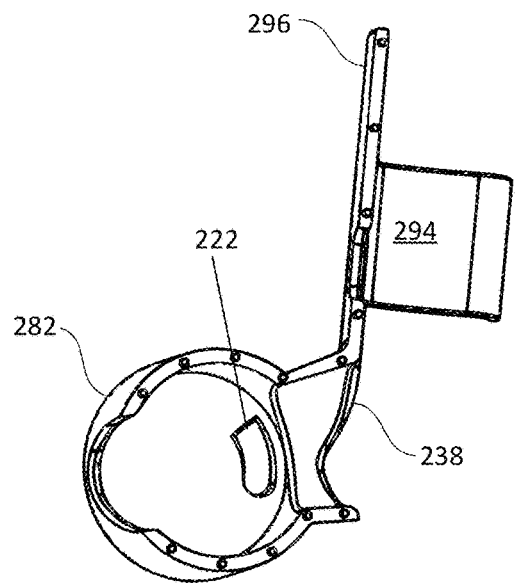

FIGS. 21A and 21B show the inner case 282 and the mounting bracket 296 in two halves. FIG. 21A shows an exterior view; FIG. 21B shows an interior view. As seen in FIG. 21A, a flexing finger 222 is cut into the side surface of the inner case 282. The flexing finger 222 has a small bump that engages with and slides within the pivot groove 220 on the inner surface of the outer case 280. As the bump slides within the pivot groove 220, it will engage with one of the two detents to hold the swivel adapter 236 in its folded-up or folded-down configuration.

Figure 22A:
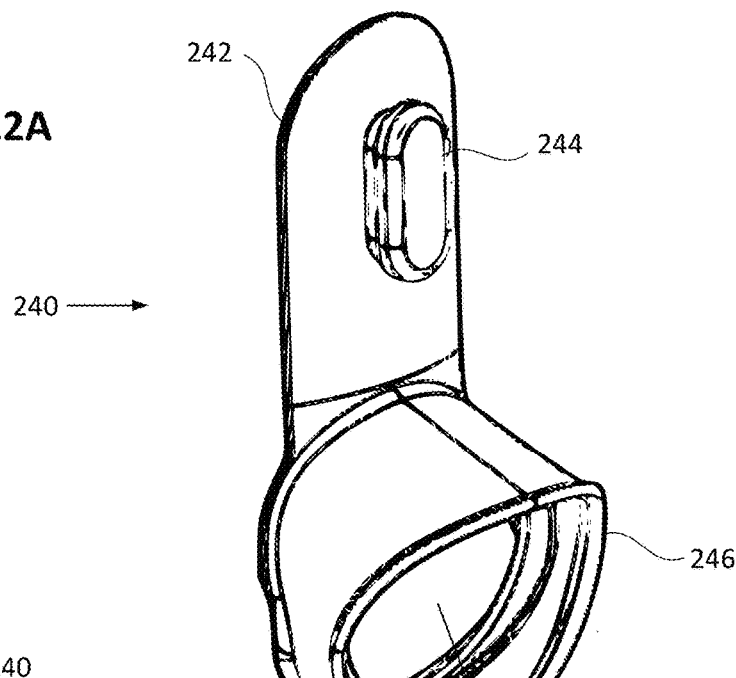
FIGS. 22A and 22B show perspective views of a silicone cushion that could be part of the spacer device.
Figure 22B:
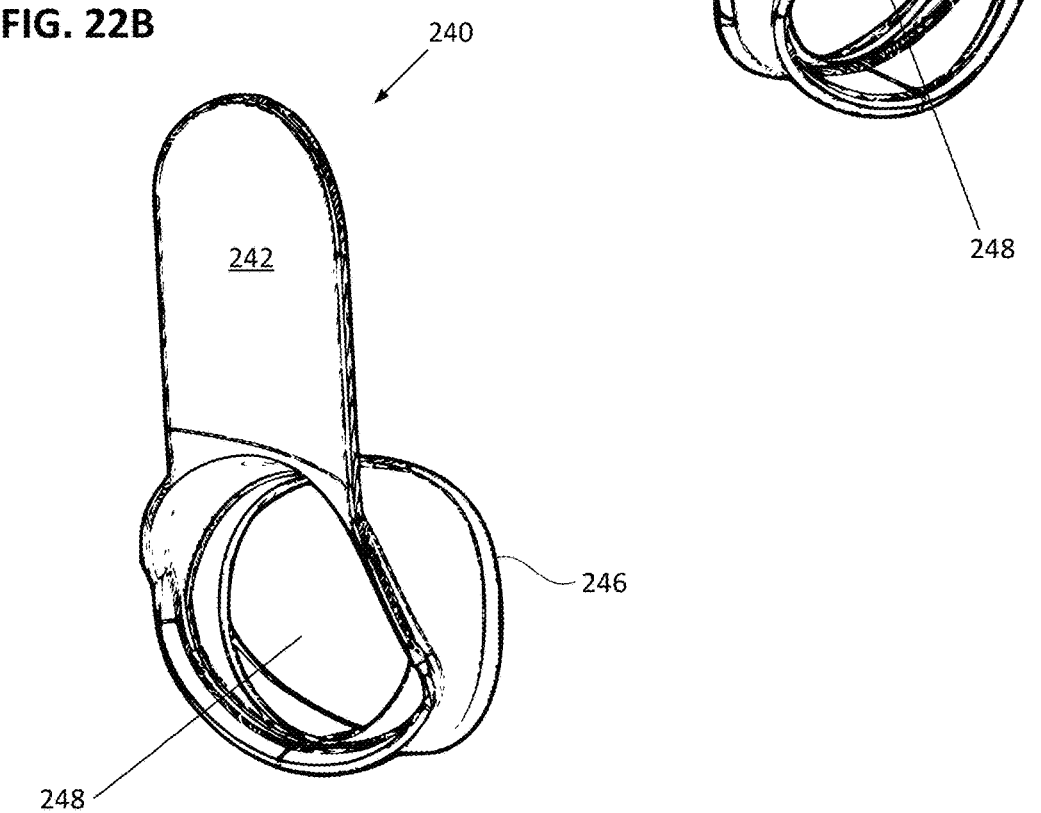

FIGS. 22A and 22B show perspective views of a silicone cushion 240 that could be part of the spacer device. The silicone cushion 240 is positioned between a support wall of a mounting bracket and the MDI. FIG. 22A shows the side facing the support wall of the mounting bracket; FIG. 22B shows the side facing the MDI. The silicone cushion 240 may be useful to dampen loose rattling of the MDI in the mounting bracket. The silicone cushion 240 here comprises a collar 246 to couple with the spray outlet of the MDI. The spray outlet of the MDI is inserted through the opening 248 of the silicone cushion 240. The silicone cushion 240 has an appendage 242 to rest against the support wall of the mounting bracket. The silicone cushion 240 also comprises a protruding mushroom head 244 on the appendage 242 to engage with a corresponding hole in the support wall of a mounting bracket. This helps retain the silicone cushion 240 against the mounting bracket.

The foregoing description and examples have been set forth merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. A spacer device for a metered dose inhaler, comprising:
    an aerosol chamber comprising a forward shell, a rear shell, and an extendable barrel in between; wherein the aerosol chamber has a compressed configuration and an extended configuration;

a mounting bracket for holding the metered dose inhaler; wherein the mounting bracket comprises a support wall that is substantially parallel and flush against the aerosol chamber;

a swivel adapter that is configured to swivel the aerosol chamber from a folded-up configuration to a folded-down configuration;

wherein the extendable barrel comprises a flexible sheath supported by a coiled wire spring; wherein the extendable barrel has a compressed configuration and an extended configuration.

2. The spacer device of claim 1, wherein the mounting bracket comprises flexing holder arms for gripping the metered dose inhaler.

3. The spacer device of claim 1, wherein the swivel adapter comprises a collar to receive a mouthpiece of the metered dose inhaler, and wherein the collar is made of a soft plastic material.

4. The spacer device of claim 1, wherein the extendable barrel has an outer diameter in the range of 2-7 cm.

5. The spacer device of claim 1, wherein the forward shell and the rear shell of the aerosol chamber are mated via a twist lock.

6. The spacer device of claim 1, wherein the length of the aerosol chamber is in the range of 3-18 cm when in the compressed configuration and in the range of 9-30 cm when in the extended configuration.

7. The spacer device of claim 1, wherein the swivel adapter comprises an inner case and an outer case that are rotatably sliding relative to each other.

8. The spacer device of claim 7, wherein the inner case has a flexing finger with a bump and the outer case has a pivot groove with two detents.

9. The spacer device of claim 8, wherein the bump on the flexing finger of the inner case engages and slides within the groove of the outer case, and the bump engages with the two detents to retain the aerosol chamber in a folded-up or folded-down configuration.

10. The spacer device of claim 1, wherein the aerosol chamber further comprises a one-way valve.

11. A medical inhaler assembly, comprising:
a spacer device of claim 1,
a metered dose inhaler comprising an actuator boot and a medication canister, wherein the actuator boot has a mouthpiece;
wherein the metered dose inhaler is held on the mounting bracket of the spacer device.

12. The medical inhaler assembly of claim 11, wherein the swivel adapter comprises a collar to receive a spray outlet of the metered dose inhaler, and wherein the mouthpiece of the metered dose inhaler is fitted into the collar.

13. The medical inhaler assembly of claim 11, wherein the aerosol chamber is aligned substantially parallel to the actuator boot of the metered dose inhaler.

14. The medical inhaler assembly of claim 11, wherein the gap between the aerosol chamber and the actuator boot of the metered dose inhaler is less than 2 cm.

15. The medical inhaler assembly of claim 11, wherein the mounting bracket comprises flexing holder arms, and wherein the actuator boot of the metered dose inhaler is held to the mounting bracket by the flexing holder arms.

16. A method of combining a metered dose inhaler with a spacer device, the method comprising:
(a) having a spacer device of claim 3;
(b) having a metered dose inhaler that comprises an actuator boot and a medication canister, wherein the actuator boot has a mouthpiece;
(c) placing the metered dose inhaler onto the mounting bracket of the spacer device;
(d) inserting the spray outlet of the metered dose inhaler into the collar of the swivel adapter.

17. The method of claim 16, wherein the aerosol chamber is aligned substantially parallel to the actuator boot of the metered dose inhaler.

18. The method of claim 16, wherein the gap between the aerosol chamber and the actuator boot of the metered dose inhaler is less than 2 cm.

19. The method of claim 16, wherein the mounting bracket comprises flexing holder arms, and wherein the actuator boot of the metered dose inhaler is held to the mounting bracket by the flexing holder arms.

20. The method of claim 16, wherein the aerosol chamber further comprises a one-way valve.

* * * * *